US011287434B2

(12) United States Patent
Niemeyer et al.

(10) Patent No.: US 11,287,434 B2
(45) Date of Patent: Mar. 29, 2022

(54) ANALYSIS SYSTEM FOR TESTING A SAMPLE

(71) Applicant: Boehringer Ingelheim Vetmedica GmbH, Ingelheim am Rhein (DE)

(72) Inventors: Axel Niemeyer, Bielefeld (DE); Hannah Schmolke, Braunschweig (DE); Heinz Schoeder, Isernhagen (DE); Kai Wuerz, Mainz (DE)

(73) Assignee: BOEHRINGER INGELHEIM VETMEDICA GMBH, Ingelheim Am Rhein (DE)

( * ) Notice: Subject to any disclaimer, the term of this patent is extended or adjusted under 35 U.S.C. 154(b) by 206 days.

(21) Appl. No.: 15/725,352

(22) Filed: Oct. 5, 2017

(65) Prior Publication Data

US 2018/0100869 A1 Apr. 12, 2018

(30) Foreign Application Priority Data

Oct. 7, 2016 (EP) .................................... 16020383

(51) Int. Cl.
*G01N 35/00* (2006.01)
*G16H 40/63* (2018.01)
*B01L 3/00* (2006.01)
*G16H 10/40* (2018.01)

(52) U.S. Cl.
CPC .. *G01N 35/00871* (2013.01); *B01L 3/502715* (2013.01); *B01L 3/545* (2013.01); *G01N 35/00029* (2013.01); *G01N 35/00732* (2013.01); *G16H 10/40* (2018.01); *G16H 40/63* (2018.01); *B01L 2200/028* (2013.01); *B01L 2200/143* (2013.01); *B01L 2300/022* (2013.01); *B01L 2300/023* (2013.01); *B01L 2300/024* (2013.01); *B01L 2300/0816* (2013.01); *G01N 35/00693* (2013.01); *G01N 2035/00752* (2013.01); *G01N 2035/00831* (2013.01); *G01N 2035/00851* (2013.01); *G01N 2035/00881* (2013.01)

(58) Field of Classification Search
None
See application file for complete search history.

(56) References Cited

U.S. PATENT DOCUMENTS

| 5,096,669 | A | 3/1992 | Lauks et al. |
| 5,961,451 | A | 10/1999 | Reber et al. |
| 6,709,869 | B2 | 3/2004 | Mian et al. |
| 7,077,328 | B2 | 7/2006 | Krishnaswamy et al. |
| 7,838,261 | B2 | 11/2010 | Gumbrecht et al. |
| 8,007,999 | B2 | 8/2011 | Holmes et al. |
| 8,580,569 | B2 | 11/2013 | Linder et al. |
| 8,950,424 | B2 | 2/2015 | Weber et al. |

(Continued)

FOREIGN PATENT DOCUMENTS

| AU | 2013201509 B2 | 11/2015 |
| DE | 20 2010 007 208 U1 | 1/2012 |

(Continued)

*Primary Examiner* — Kathryn Wright
(74) *Attorney, Agent, or Firm* — David S. Safran; Roberts Calderon Safran & Cole, P.C.

(57) ABSTRACT

An analysis system and a method for testing a biological sample, wherein an operating instrument is provided which preferably can be separated from an analysis device with respect to a data connection and/or wirelessly connected to the analysis device.

11 Claims, 4 Drawing Sheets

(56) References Cited

U.S. PATENT DOCUMENTS

| | | | |
|---|---|---|---|
| 9,110,044 B2 | 8/2015 | Gumbrecht et al. | |
| 9,186,278 B2 | 11/2015 | Baym et al. | |
| 9,686,395 B2 | 6/2017 | Erickson et al. | |
| 9,810,704 B2 | 11/2017 | Holmes et al. | |
| 9,841,421 B2 | 12/2017 | Dittmer et al. | |
| 10,073,590 B2 | 9/2018 | Dascola et al. | |
| 2005/0047973 A1 | 3/2005 | Schulz et al. | |
| 2006/0264782 A1* | 11/2006 | Holmes | G01N 21/76 600/583 |
| 2006/0292039 A1 | 12/2006 | Iida | |
| 2008/0207461 A1 | 8/2008 | Ermantraut et al. | |
| 2008/0240983 A1 | 10/2008 | Harris | |
| 2009/0145753 A1* | 6/2009 | Yang | G01N 33/48771 204/403.01 |
| 2011/0253224 A1* | 10/2011 | Linder | G01N 21/59 137/2 |
| 2012/0123686 A1* | 5/2012 | Xiang | G16H 40/63 702/19 |
| 2014/0052400 A1 | 2/2014 | Ogura | |
| 2014/0335505 A1 | 11/2014 | Holmes | |
| 2015/0099306 A1 | 4/2015 | Ku | |
| 2015/0346097 A1 | 12/2015 | Battrell et al. | |
| 2018/0141038 A1 | 5/2018 | Van Der Zaag et al. | |

FOREIGN PATENT DOCUMENTS

| | | |
|---|---|---|
| WO | 2006121510 A2 | 11/2006 |
| WO | 2014160861 A1 | 10/2014 |

* cited by examiner

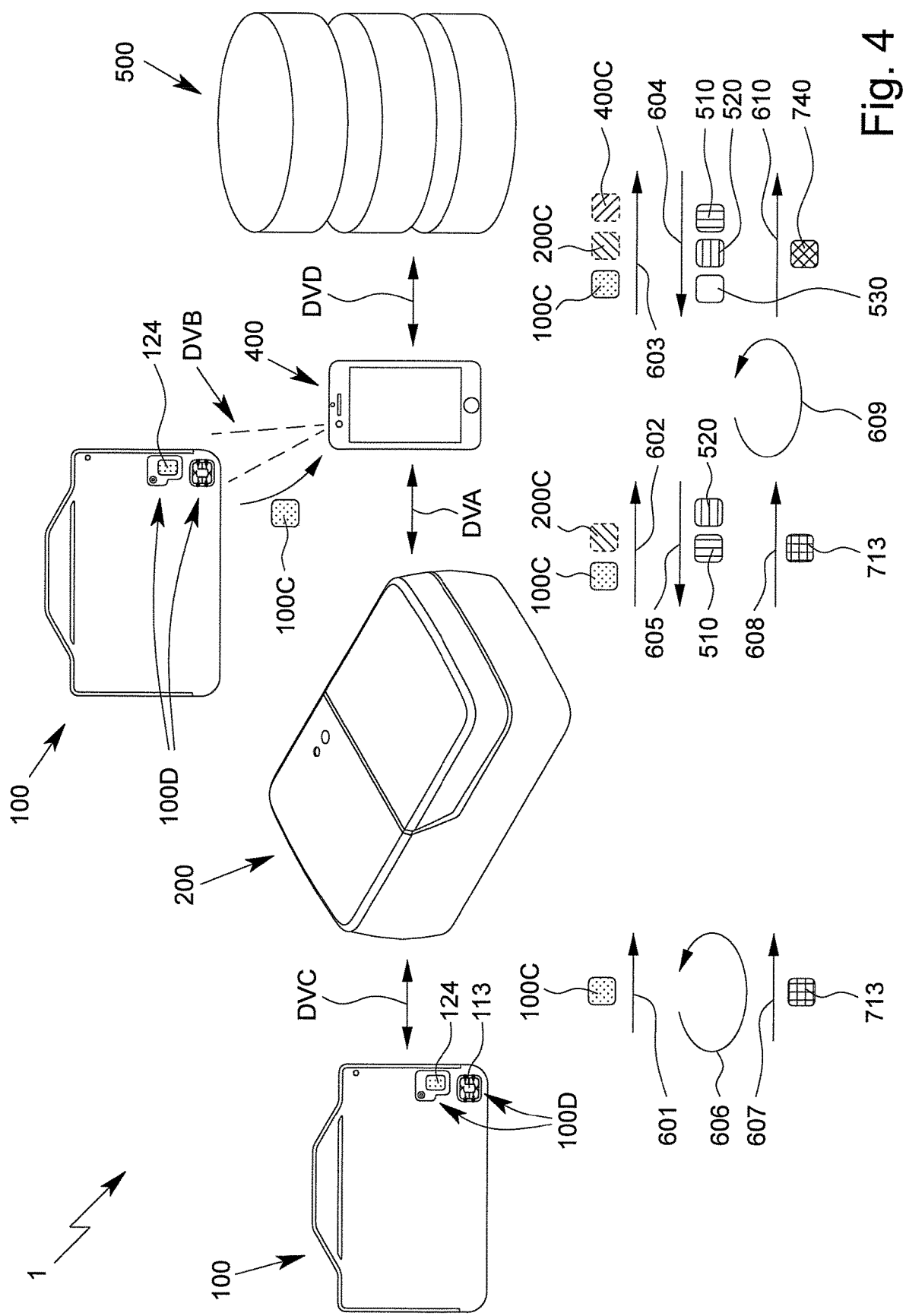

ANALYSIS SYSTEM FOR TESTING A SAMPLE

BACKGROUND OF THE INVENTION

Field of the Invention

The present invention relates to an analysis system for testing a biological sample.

Preferably, the present invention deals with analyzing and testing a sample, in particular, from a human or animal, particularly preferably for analytics and diagnostics, for example with regard to the presence of diseases and/or pathogens and/or for determining blood counts, antibodies, hormones, steroids or the like. Therefore, the present invention is in particular within the field of bioanalytics. A food sample, environmental sample or another sample may optionally also be tested, in particular for environmental analytics or food safety and/or for detecting other substances.

Preferably, by means of the present invention, at least one analyte (target analyte) of a sample can be determined, identified or detected. In particular, the sample can be tested for qualitatively or quantitatively determining at least one analyte, for example in order for it to be possible to detect or identify a disease and/or pathogen.

Within the meaning of the present invention, analytes are in particular nucleic-acid sequences, in particular DNA sequences and/or RNA sequences, and/or proteins, in particular antigens and/or antibodies. In particular, by means of the present invention, nucleic-acid sequences can be determined, identified or detected as analytes of a sample, and/or proteins can be determined, identified or detected as analytes of the sample. More particularly preferably, the present invention deals with systems, devices and other apparatus for carrying out a nucleic-acid assay for detecting or identifying a nucleic-acid sequence and/or a protein assay for detecting or identifying a protein.

The present invention deals in particular with what are known as point-of-care systems, i.e., in particular with mobile systems, devices and other apparatus, and deals with methods for carrying out tests on a sample at the sampling site and/or independently and/or away from a central laboratory or the like. Preferably, point-of-care systems can be operated autonomously of and/or independently from a mains network for supplying electrical power.

Description of Related Art

U.S. Pat. No. 5,096,669 discloses a point-of-care system for testing a biological sample, in particular a blood sample. The system comprises a single-use cartridge and an analysis device. Once the sample has been received, the cartridge is inserted into the analysis device in order to carry out the test. The cartridge comprises a microfluidic system and a sensor apparatus comprising electrodes, which apparatus is calibrated by means of a calibration liquid and is then used to test the sample.

Furthermore, International Patent Application Publication WO 2006/125767 A1 and corresponding U.S. Pat. No. 9,110,044 disclose a point-of-care system for integrated and automated DNA or protein analysis, comprising a single-use cartridge and an analysis device for fully automatically processing and evaluating molecular-diagnostic analyses using the single-use cartridge. The cartridge is designed to receive a sample, in particular blood, and in particular allows cell disruption, PCR and detection of PCR amplification products, which are bonded to capture molecules and provided with a label enzyme, in order for it to be possible to detect bonded PCR amplification products or nucleic sequences as target analytes in what is known as a redox cycling process.

German Patent DE 100 58 394 C1 and corresponding U.S. Pat. No. 7,838,261 disclose a method for testing a sample using a reaction array comprising at least two reaction compartments for receiving substances that react with one another, the reaction compartments being interconnected by means of a supply space. In order to measure the substances, an exchange of substances and thus chemical crosstalk between the individual reaction compartments is prevented by lowering a sensor cover. In this way, the detection sensitivity of the method is increased.

European Patent Application EP 2 305 383 B1 and corresponding U.S. Patent Application Publication 2008/207461 A1 disclose an instrument for carrying out and analyzing microarray experiments. In particular, this document discloses carrying out microarray experiments in parallel in order to detect specific interactions between probe molecules and target molecules in a microtiter plate. In this case, probes in the form of a substance library are provided on carriers, and therefore a sample can be simultaneously analyzed on a plurality of probes in parallel. In the context of microarray experiments of this kind, it is also disclosed that a desired operating mode can be specified for a processing apparatus externally, in particular by a user.

U.S. Patent Application Publication US 2011/0253224 A1 discloses a feedback control in microfluidic systems. The control of fluids involves the use of feedback from one or more processes or events taking place in the microfluidic system. For instance, a detector may detect one or more fluids at a measurement zone and, using this data, a control system may determine whether to modulate subsequent fluid flow in the microfluidic system.

U.S. Patent Application Publication US 2015/0148705 A1 discloses systems and devices for sampling and profiling microbiota of skin. A microbe profiling device includes a handheld housing with an elongated flexible strip including a microbe-capture region and a location information storage component. The strip is configured to capture microbes from one or more regions of a skin surface of an individual, and the location information storage component is configured to store information associated with the location of said one or more regions.

U.S. Patent Application Publication US 2014/0296089 A1 discloses systems and methods for multi-analysis and sample processing. A device may be provided, capable of receiving the sample, and performing one or more of a sample preparation, sample assay, and detection step. The device may be capable of performing multiple assays.

German Utility Model DE 20 2010 007 208 U1 discloses a device for testing of body fluids applied to carrier materials. The device comprises at least two apparatus for determining different substances present in the body fluid, wherein the carrier materials to be inserted into the device are provided with a coding specific to the relevant body fluid and substance to be determined. The relevant apparatus can be activated via the corresponding coding. Furthermore, an additional external device can be provided to evaluate and to present measurement results.

U.S. Patent Application Publication US 2002/0060247 A1 discloses an analyte test instrument system including data management system and a method of managing data for a plurality of analyte test instruments connect to a data communication network. The method comprises the steps of:

detecting via a host computer, the connection of each instrument to the data communication network; uploading data received from each instrument to the host computer; processing the uploaded data on the host computer for operator review; and downloading configuration data from the host computer to each test instrument, the downloaded data comprising instruments specific setup and control data.

Australian Patent Application Publication AU 2013 201509 B2 discloses Point-of-Care fluidic systems and uses thereof. Specifically, the invention provides portable medical devices that allow real-time detection of analytes from a biological fluid. A system for detecting an analyte in a bodily fluid comprises a fluidic device in which a sample of bodily fluid can react with reactants contained within the device, based on a protocol transmitted from an external device, to yield a detectable signal indicative of the presence of said analyte. The system further comprises a reader assembly for detecting said detectable signal. The external device is external to the reader assembly and stores a plurality of protocols, wherein the reader assembly is configured to download a fluidic device-specific protocol selected from the plurality of protocols on the external device to run on the fluidic device based on an identity of the fluidic device.

U.S. Pat. No. 5,961,451 A discloses a non-invasive apparatus having a retaining member to retain a removable biosensor. The apparatus includes a non-invasive extraction device to non-invasively extract a biological sample from an end-user, preferably through the skin by transdermal permeation. The apparatus further comprises a biosensor to sense a characteristic, property, or parameter of the biological sample.

U.S. Patent Application Publication US 2006/0292039 A1 discloses a measuring system making it possible for a user to check his/her own health state at a desired place without visiting inspection agencies. First, a user collects body fluid which is introduced to a chip as a sample. The sample is made to act on a detection reagent which acts on a specific component in the sample to generate a predetermined detection reaction. The chip is set to a mobile terminal, which measures an amount of a specific component in the sample. The mobile terminal transmits the measurement value to an analysis center.

U.S. Patent Application Publication US 2015/0244852 A1 discloses an apparatus and method for Point-of-Collection measurement of a biomolecular reaction. A biological sample is collected on a modular diagnostic test platform, which is inserted into a smartphone accessory. Optical, electrical, mechanical, or other means are used to transduce a biomolecular binding event and communicate the results with the smartphone. The result can then be presented quantitatively, displayed to the user, stored for later comparison, and communicated to a central hub location where medical professionals can provide additional review.

SUMMARY OF THE INVENTION

The problem addressed by the present invention is to provide an analysis system, a method and a computer program product for evaluating a sample, it being possible to test the sample and/or to test measurement results in a more efficient, individual and/or flexible manner.

The above problem is solved by an analysis system as described herein.

A proposed analysis system is provided for testing, in particular, a biological sample.

The analysis system is in particular portable, mobile and/or is a point-of-care system and/or is or can be operated autonomously, in particular independently from a power network, in particular at the sampling site and/or away from a central laboratory and/or by means of a power storage unit.

The analysis system preferably comprises an analysis device and a cartridge for testing the sample, the cartridge preferably being designed for receiving the sample. Particularly preferably, the analysis device is designed to receive the cartridge or to connect said cartridge electrically, thermally and/or pneumatically. The analysis device is preferably designed to subsequently carry out the test using the received cartridge. For this purpose, the cartridge can be inserted or loaded into the analysis device, whereupon the analysis device can act on the cartridge in order to carry out the test.

Channels in which the sample can be conveyed are preferably provided in said cartridge. This makes it possible for the sample to be pretreated or processed on the card and/or for the sample to be evaluated or analyzed by means of a sensor apparatus, which is preferably also located on the card.

Particularly preferably, the analysis system comprises an operating instrument. This operating instrument may be or comprise a smartphone, tablet or the like. Therefore, the operating instrument is in particular a portable and/or mobile (terminal) device.

It is preferable for the operating instrument to be separable or separated from the analysis device physically and/or with respect to a data connection. This can be achieved, for example, by disconnecting or terminating or breaking a data connection between the analysis device and the operating instrument, in particular manually or by removing the operating instrument from the analysis device.

Alternatively, or additionally, it is provided for the operating instrument to be connectable or connected to the analysis device wirelessly and/or via a radio connection or air interface. Particularly preferably, the operating instrument can be or is automatically connected to and/or disconnected and/or separated from the analysis device with respect to a data connection, in particular via what is known as an ad-hoc data connection or an ad-hoc network, such as a Bluetooth connection, which is established and/or configured automatically. In addition to the Bluetooth standard, other conventional short-range transmission methods, NFC, WPAN or WLAN are also suitable.

By means of the operating instrument, it is preferably possible to achieve the configurations of the analysis device required for the test, and therefore it is not necessary for the analysis device to comprise any complex user interfaces, but rather the analysis device preferably comprises, at most, an on-off switch and a rudimentary status display (not comprising a screen or the like). This advantageously makes it possible to use standard hardware that can be configured in a flexible manner, such as smartphones or tablets, in order for a user-friendly configuration to be achieved, enabling or facilitating a flexibility with regard to the embodiment of the operating instrument and for corresponding data and interfaces to be updated in a simple and software-based manner.

In this respect, one aspect of the present invention is that the operating instrument is preferably designed to determine, read out or receive a cartridge identifier corresponding to the cartridge and, using the cartridge identifier, to retrieve from a database control information for carrying out the test, which information is in particular specific to the cartridge or a batch to which the cartridge is assigned, and/or to transmit said information to the analysis device.

This aspect is advantageous in that it is thus possible to use control information that is individual, unique and/or specific to the specific cartridge. This control information can incorporate characteristic features of the specific cartridge or a batch of cartridges, relating for example to the substances therein, to the suitability for a certain test, to the use of certain sensor arrangements, or to specific information for carrying out the test, wherein the information is adapted to the cartridge, the batch or the like, and contains, for example, adapted times, temperatures or the like.

In this regard, the use of the operating instrument that can be separated and/or disconnected from the analysis device and/or wirelessly connected to the analysis device is particularly advantageous in that the cartridge or the cartridge batch can be identified in a simple manner and independently from the analysis device, and corresponding control information can, separately and/or disconnected from the analysis device, also be retrieved and/or stored temporarily, for example in advance. The control information can then be transmitted to the analysis device at a later stage, also independently from a link between the operating instrument and the Internet and/or the database.

According to another aspect of the present invention, which can also be implemented independently, the operating instrument is preferably designed to transmit to the analysis device control information for carrying out the test supported by the cartridge, which information is in particular specific to the cartridge or a batch to which the cartridge is assigned, the analysis device being designed to carry out the test using the transmitted control information independently from and/or separately and/or disconnected from the operating instrument.

It is therefore preferable for the analysis system to be configured by the operating instrument to such an extent that the test of the in particular biological sample using the cartridge can be started or has been started by the analysis device. It is then not necessary for the operating instrument to remain permanently connected to the analysis device, and therefore the operating instrument can be used in a manner in which it is separated and/or disconnected from the analysis device with respect to a data connection.

This makes it possible to handle and use the operating instrument in a flexible manner and independently from the analysis device, in particular in cases where the sample is tested for a prolonged period of time. Another advantage is that the analysis device can operate autonomously following corresponding configuration, and therefore the proper testing of the sample is not dependent on the maintenance of the radio connection between the operating instrument and the analysis device, which may be subject to disturbance, but rather the test can advantageously be carried out in a very robust, reliable and disturbance-resistant manner as a result of the test not being dependent on the maintenance of the radio connection.

According to another aspect of the present invention, which can also be implemented independently, the analysis device is designed to receive control information from the operating instrument, which information is in particular specific to the cartridge or a batch to which the cartridge is assigned, to control the testing of the sample in the cartridge using the control information, and to transmit measurement results determined during the test to the operating instrument without any prior evaluation.

It is therefore preferable for the measurement results to be interpreted outside the analysis device, particularly preferably by the operating instrument. Alternatively, evaluation can, however, also take place externally, for which purpose the operating instrument can send the measurement results to a server for example. The analysis device is preferably not set up to directly interpret the measurement results from the test of the sample.

Advantageously, interpreting the measurement results outside the analysis device, in particular by means of the operating instrument, is advantageous in that the evaluation methods can be dynamically adapted without having to make any changes to the analysis device. This is particularly advantageous in the context of the present analysis system based on cartridges which are separated from the analysis device in an initial state and are inserted into the analysis device for carrying out the tests.

In this regard, the present system provides the flexibility of using different cartridges in order to carry out different tests on different samples. Different measurement results can then in turn be interpreted in different ways. Adapting an analysis device to variable conditions of this kind is complex and may require that the hardware, after some time, be replaced because the processing capacity is too low or because of some other adaptation requirement, even though the mechanical components of the analysis device might not actually need to be replaced.

Consequently, it has been found to be particularly advantageous for the analysis device to be physically separated from the operating instrument and for the measurement results to be evaluated outside the analysis device by means of the operating instrument or via the operating instrument, in particular since the operating instrument can be replaced in a simpler and more cost-effective manner and also at more frequent intervals without the complex mechanical system of the analysis device for carrying out the test using the cartridge also having to be exchanged.

Another aspect of the present invention, which can also be implemented independently, likewise relates to the evaluation of the measurement results. In this respect, it is preferable for the operating instrument to be designed to determine, read out or receive a cartridge identifier corresponding to the cartridge and, using the cartridge identifier, to retrieve from a database evaluation infoiivation designed for evaluating measurement results determined during the test, which information is in particular specific to the cartridge or a batch to which the cartridge is assigned, and to evaluate the measurement results using the evaluation information independently and/or separately and/or disconnected from the analysis device.

In this regard, it is advantageous that, by identifying the cartridge using the cartridge identifier, it is possible to use evaluation information which is individual or unique to the cartridge or the cartridge batch. In this respect, it is possible to take into account properties of the sample preparation, the cartridge, the environmental conditions and/or the sensor arrangement or other information that is specific to the cartridge and conducive to rapid and/or reliable evaluation of the measurement results.

Further advantages have already been explained in the context of the measurement results being evaluated externally outside the analysis device, to which reference is made.

Another advantage is that the measurement results can be evaluated in the operating instrument in an individual and correspondingly accurate manner. If the evaluation information is retrieved from the database in advance and initially stored temporarily in the operating instrument, as is the case in a preferred embodiment, despite the flexible hardware there is thus no need for a connection to the Internet or other servers and/or databases for the purpose of evaluating the measurement results.

This is particularly advantageous in connection with the fact that the proposed analysis system is preferably a point-of-care system for use on site, i.e., in the surroundings of the sampling site. In case of doubt, the proposed analysis system is used for example in the countryside in a pigsty or on a mountainous pasture where infrastructural weak points can typically lead to mobile communication connections or the like not being reliably available. In this case, it is particularly advantageous for the measurement results to be evaluated in the operating instrument outside of and separately and/or disconnected from the analysis device.

The present invention also relates to a method for testing an in particular biological sample by means of the analysis system comprising the cartridge, the analysis device for receiving the cartridge and the operating instrument, which is preferably separable and/or disconnectable from the analysis device with respect to a data connection and/or wirelessly connectable to the analysis device with respect to a data connection.

According to one aspect of the proposed method, which can also be implemented independently, a cartridge identifier corresponding to the cartridge is determined, read out or received by the operating instrument. Using the cartridge identifier, control information is retrieved from a database and/or transmitted to the analysis device. In this case, the control information is preferably specific to the cartridge or a batch with which the cartridge is associated, the cartridge or batch corresponding to the cartridge identifier. Furthermore, the control information is designed to control the analysis device in order to carry out the test using the cartridge. As a result, the advantages that have already been explained at the outset can be achieved.

In another aspect of the proposed method, which can also be implemented independently, the operating instrument transmits control information to the analysis device, the control information preferably being specific to the cartridge or a batch with which the cartridge is associated and/or being suitable for carrying out the test supported by the cartridge. Furthermore, the analysis device carries out the test using the transmitted control information independently and/or separately and/or disconnected from the operating instrument. As a result, the advantages that have already been explained at the outset can be achieved.

According to another aspect of the proposed method, which can also be implemented independently, the analysis device receives the control information from the operating instrument, which information is preferably specific to the cartridge and/or batch. The analysis device controls the testing of the sample in the cartridge using the control information. The measurement results determined during the test are transmitted to the operating instrument without any prior evaluation. As a result, the advantages that have already been explained at the outset can be achieved.

According to another aspect of the proposed method, which can also be implemented independently, the operating instrument determines, reads out or receives a cartridge identifier corresponding to the cartridge or batch. Using the cartridge identifier, evaluation information, which is preferably specific to the cartridge or batch, is retrieved from a database, which evaluation information is suitable or designed for evaluating measurement results determined during the test. Using the evaluation information, the measurement results are evaluated independently and/or separately and/or disconnected from the analysis device. As a result, the advantages that have already been explained at the outset can be achieved.

As a result, a data connection between the operating instrument and the analysis device may be provided initially. Subsequently, control information is preferably transmitted to the analysis device. In this case, the control information preferably corresponds to a cartridge, which can be or is loaded into the analysis device, or to a batch with which the cartridge is associated. Using the control information, testing of a sample received in the cartridge is preferably started. After the test has begun, the operating instrument can be separated and/or disconnected from the analysis device or the operating instrument is separated and/or disconnected from the analysis device and the test is continued, preferably brought to an end, by means of the analysis device comprising the cartridge and independently from the operating instrument. Subsequently, a measurement result, as the result of the test, can be transmitted to the operating instrument. If the operating instrument has previously been separated and/or disconnected from the analysis device, the measurement results are preferably transmitted automatically once the operating instrument has been reconnected to the analysis device and/or a data connection between the operating instrument and the analysis device has been re-established.

According to another aspect of the present invention, which can also be implemented independently, the analysis device receives from the operating instrument the control information specific to the cartridge. The analysis device controls the testing of the sample in the cartridge using the control information. The measurement results determined during the test are transmitted to the operating instrument without any prior evaluation.

According to another aspect of the present invention, which can also be implemented independently, the operating instrument determines, reads out or receives an identifier corresponding to the cartridge. Using the identifier, evaluation information specific to the cartridge is retrieved from a database, which evaluation information is suitable or designed for evaluating measurement results determined during the test. Using the evaluation information, the measurement results are evaluated independently and/or separately and/or disconnected from the analysis device.

Another aspect of the present invention, which can also be implemented independently, relates to a computer program product comprising program code means which, when executed, for example, by a processor, computer, microcontroller or one or more other data processing apparatus for executing the program code means, in particular of the operating instrument and/or the analysis device, cause the method steps or the method according to the present invention to be carried out.

The term "analysis device" is preferably understood to mean an instrument which is in particular mobile and/or can be used on site, and/or which is designed to chemically, biologically and/or physically test and/or analyze a sample or a component thereof, preferably in and/or by means of a cartridge. In particular, the analysis device controls the pretreatment and/or testing of the sample in the cartridge. For this purpose, the analysis device can act on the cartridge, in particular such that the sample is conveyed, temperature-controlled and/or measured in the cartridge.

The term "cartridge" is preferably understood to mean a structural apparatus or unit designed to receive, to store, to physically, chemically and/or biologically treat and/or prepare and/or to measure a sample, preferably in order to make it possible to detect, identify or determine at least one analyte, in particular a protein and/or a nucleic-acid sequence, of the sample.

A cartridge within the meaning of the present invention preferably comprises a fluid system having a plurality of channels, cavities and/or valves for controlling the flow through the channels and/or cavities.

In particular, within the meaning of the present invention, a cartridge is designed to be at least substantially planar, flat and/or card-like, in particular is designed as a (micro)fluidic card and/or is designed as a main body or container that can preferably be closed and/or said cartridge can be inserted and/or plugged into a proposed analysis device when it contains the sample.

The term "operating instrument" is preferably understood to mean an apparatus by means of which the analysis device can be controlled, control information can be transmitted to the analysis device, and/or measurement results can be received from the analysis device and/or measurement results can be evaluated. Preferably, the operating instrument is or forms a user interface for controlling the test and/or the evaluation or outputting of measurement results.

The operating instrument can alternatively be called operator control instrument. The operating instrument preferably is configured to be operated by an operator (user) for controlling, in particular of the analysis device, the test and/or the evaluation. Thus, the operating instrument is or comprises a user interface for input of commands and transfer of pieces of control information to the analysis device.

The operating instrument preferably comprises an input apparatus for controlling the analysis device, for controlling data transmission and/or for controlling the evaluation of measurement results. Alternatively, or additionally, the operating instrument comprises an output apparatus for outputting, in particular displaying, information, in particular status information, operating elements and/or results. The operating instrument preferably comprises a processor, microcontroller and/or memory for executing a computer program product for data transmission, for control and/or for evaluating measurement results.

Particularly preferably, the operating instrument is a mobile terminal device, in particular for a radio and/or mobile network, such as a smartphone, tablet computer, mobile telephone or the like. The operating instrument can preferably be operated independently from a power network, using a power storage means, in particular a (rechargeable) battery, and in a mobile manner, autonomously of and/or independently from further components of the analysis system, in particular the analysis device. The operating instrument preferably comprises one or more interfaces for wireless data communications, in particular a WPAN communication interface, a WLAN communication interface, a near-field communication interface, an optical communication interface such as a camera, and/or a mobile radio interface.

The term "test" as used herein preferably means a test procedure/sequence and/or performing an assay, in particular one, several or all steps for performing an assay to determine one or more analytes of a sample. The steps are preferably realized by or within the analysis system, analysis device and/or cartridge.

An "assay" according to the present invention is preferably an investigative procedure for qualitatively and/or quantitatively measuring, detecting and/or identifying the presence, amount, and/or functional activity of a target entity or analyte of the sample. The analyte can, e.g., be a drug, a biological, chemical and/or biochemical substance, and/or a cell in an organism or organic sample. In particular, the analyte can be a molecule, a nucleic-acid sequence, a DNA, an RNA and/or a protein.

Preferably, the assay according to the present invention is a nucleic-acid assay for detecting or identifying a nucleic-acid sequence and/or a protein assay for detecting or identifying a protein.

An assay, test or test procedure according to the present invention accordingly preferably covers at least one of: controlling actuators of the analysis device like a pump drive, temperature control apparatus, and valve actuators; acting on the cartridge or sample; treating the sample; preparing the sample; performing one or more mixing processes and/or reactions with the sample; conveying the sample; and measuring one or more properties of the sample, particularly with the sensor apparatus of the cartridge.

The sensor apparatus or a sensor array thereof preferably comprises multiple sensor fields and/or electrodes for specifically bonding and/or detecting one or more analytes to be detected or measured. Further, the sensor apparatus preferably is configured for electrical or electrochemical detection of analytes of the sample.

Alternatively, or additionally, the sensor apparatus and/or the sensor device can be configured for detecting or measuring other or further analytes compounds, material characteristics, or the like without specific bonding and/or by means of optical measurement, impedance measurement, capacitance measurement, spectrometric measurement, mass spectrometric measurement, or tomography like MRT. In this regard, the sensor apparatus, thus, can be formed by an arrangement enabling such measurement. In particular, the sensor apparatus or cartridge or any other sample carrier of the analysis device or system can comprise or form a cavity having a window for said optical measurement. The optical sensor or the sensor apparatus, such as a spectrometer, can be realized independently of the cartridge and/or can form part of the analysis device.

In the following, the present invention is explained based primarily on the sensor apparatus having multiple sensor fields and/or being or comprising a chip having electrodes for electrochemical detection. However, unless stated or conductible unambiguously to the contrary, it is to be understood that measurement results alternatively or additionally can be achieved by or can be the outcome of one or more of the above mentioned measurement techniques even if not mentioned explicitly.

An assay, test or test procedure according to the present invention preferably starts or begins with the analysis device acting on and/or controlling processes on the cartridge and/or the sample. In particular, a test starts or begins with actuators acting on the cartridge. For example, a test can start with conveying the sample within the cartridge.

Methods and/or steps performed before insertion or receiving of the cartridge into/by the analysis device and/or before conveying, treating and/or preparing the sample within said cartridge are preferably not part of an assay, test or test procedure according to the present invention.

The "control information", thus, preferably is configured to carry out such an assay, test or test procedure or to enable the analysis system or the analysis device to carry out such an assay, test or test procedure. Preferably, said control information is configured to control or to define a control sequence or to be used by the analysis device to carry out said assay, test or test procedure. A "control information", thus, preferably has instructions being configured for controlling the assay, test or test procedure. In particular, the control information is configured to control an assay, test or test procedure by defining steps or parameters of steps including controlling and/or feedback controlling actuators like the pump drive, the temperature control apparatus and valve actuators.

The above-mentioned aspects and features of the present invention and the aspects and features of the present invention that will become apparent from the claims and the following description can in principle be implemented independently from one another, but also in any combination or order.

Other aspects, advantages, features and properties of the present invention will become apparent from the following description of a preferred embodiment with reference to the accompanying drawings.

BRIEF DESCRIPTION OF THE DRAWINGS

FIG. 4 shows a schematic sequence using the analysis system.

DETAILED DESCRIPTION OF THE INVENTION

In the figures, which are only schematic and sometimes not to scale, the same reference signs are used for the same or similar parts and components, corresponding or comparable properties and advantages being achieved even if these are not repeatedly described.

Figure 1:
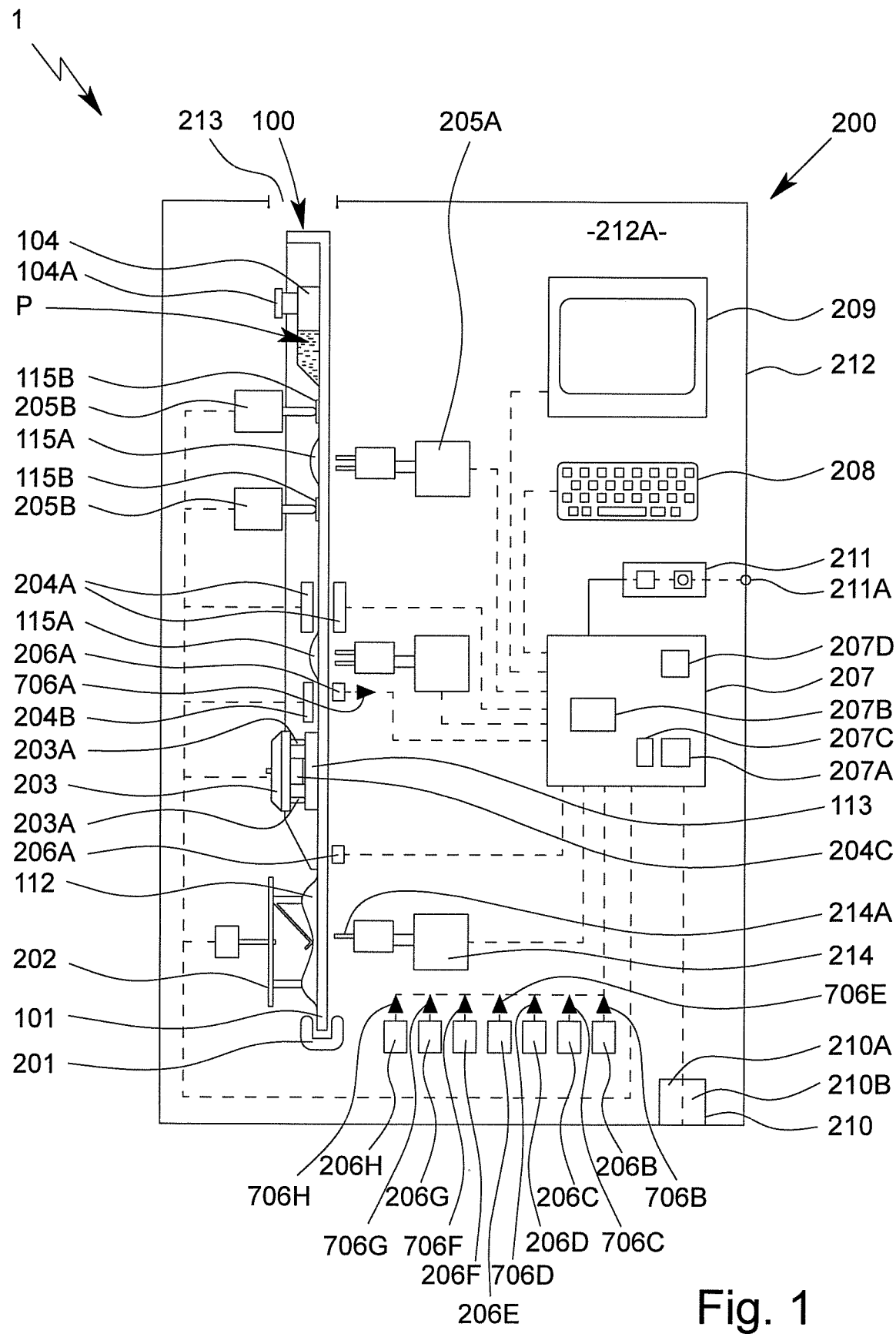
FIG. 1 is a schematic view of a proposed analysis system and/or analysis device comprising a proposed cartridge received therein.

FIG. 1 is a highly schematic view of a proposed analysis system 1 and analysis device 200 for testing an in particular biological sample P, preferably by means of or in an apparatus or cartridge 100.

Figure 2:
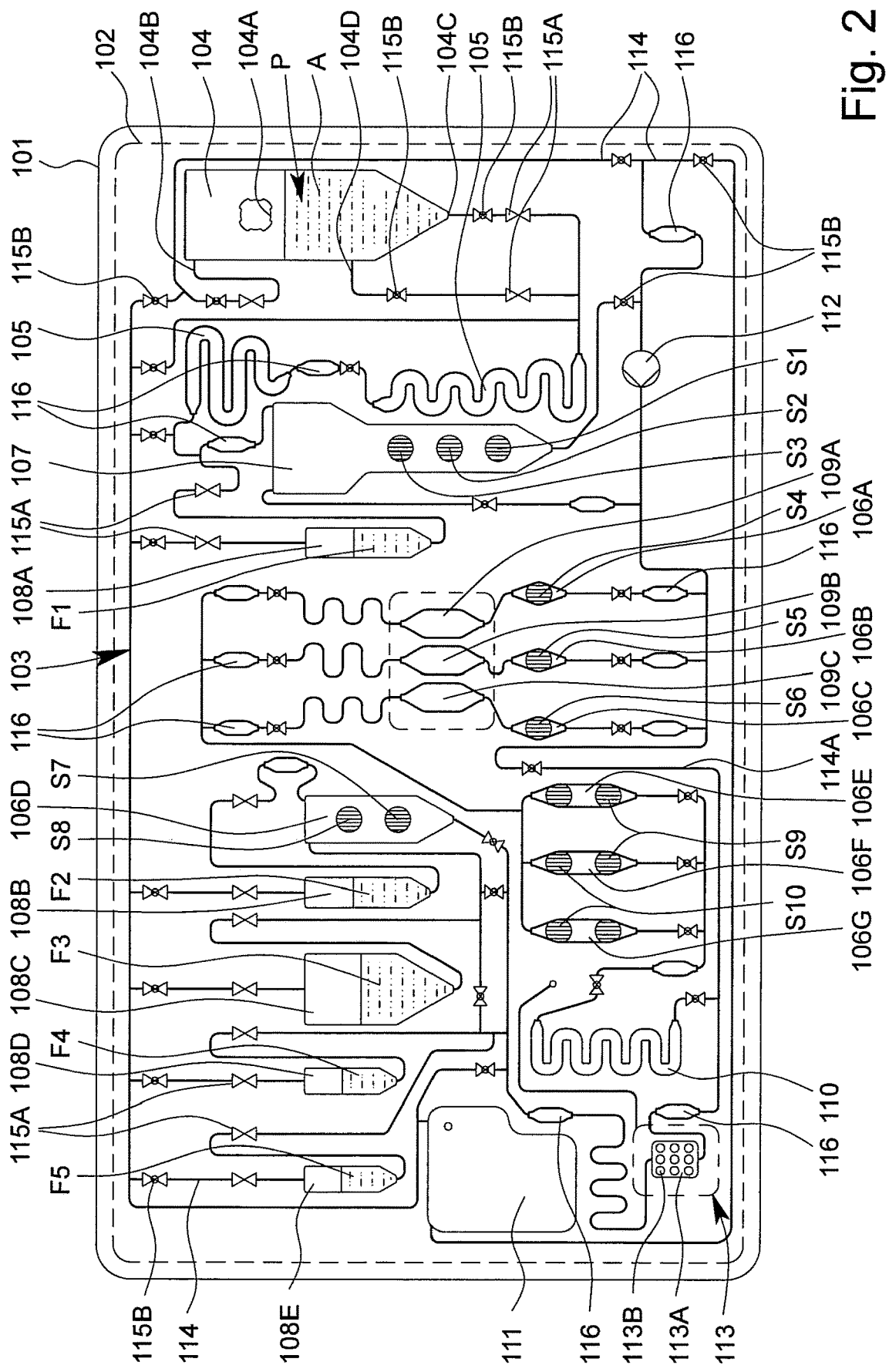
FIG. 2 is a schematic view of the cartridge.

FIG. 2 is a schematic view of a preferred embodiment of the proposed apparatus or cartridge 100 for testing the sample P. The apparatus or cartridge 100 in particular forms a handheld unit, and in the following is merely referred to as a cartridge.

The term "sample" is preferably understood to mean the sample material to be tested, which is in particular taken from a human or animal. In particular, within the meaning of the present invention, a sample is a fluid, such as saliva, blood, urine or another liquid, preferably from a human or animal, or a component thereof. Within the meaning of the present invention, a sample may be pretreated or prepared if necessary, or may come directly from a human or animal or the like, for example. A food sample, environmental sample or another sample may optionally also be tested, in particular for environmental analytics, food safety and/or for detecting other substances, preferably natural substances, but also biological or chemical warfare agents, poisons or the like.

Preferably, the analysis system 1 and/or analysis device 200 controls the testing of the sample P in particular in or on the cartridge 100 and/or is used to evaluate the testing and/or to collect, to process and/or to store measurement results from the test.

The analysis system 1 preferably comprises one or more cartridges 100 for receiving the sample P. The analysis system 1 preferably comprises the analysis device 200 for receiving the cartridge 100 and subsequently carrying out the test using the received cartridge 100.

By means of the proposed analysis system 1, analysis device 200 and/or cartridge 100 and/or using the proposed method for testing the sample P, preferably an analyte A of the sample P, in particular a (certain) nucleic-acid sequence and/or a (certain) protein, or particularly preferably a plurality of analytes A of the sample P, can be determined, identified or detected. Said analytes A are in particular detected, identified and/or measured not only qualitatively, but particularly preferably also quantitatively.

Therefore, the sample P can in particular be tested for qualitatively or quantitatively determining at least one analyte A, for example in order for it to be possible to detect a disease and/or pathogen or to determine other values, which are important for diagnostics, for example.

Particularly preferably, a molecular-biological test is made possible by means of the analysis system 1 and/or analysis device 200 and/or by means of the cartridge 100.

Particularly preferably, a nucleic-acid assay for detecting a nucleic-acid sequence, in particular a DNA sequence and/or RNA sequence, and/or a protein assay for detecting a protein, in particular an antigen and/or antibody, are made possible or are carried out.

Preferably, the sample P or individual components of the sample P or analyte A can be amplified if necessary, in particular by means of PCR, and tested, identified or detected in the analysis system 1, analysis device 200 and/or in the cartridge 100, and/or for the purpose of carrying out the nucleic-acid assay. Preferably, amplification products of the analyte A or analytes A are thus produced.

In the following, further details are first given on a preferred construction of the cartridge 100, with features of the cartridge 100 preferably also directly representing features of the analysis system 1, in particular even without any further explicit explanation.

The cartridge 100 is preferably at least substantially planar, flat, plate-shaped and/or card-shaped.

The cartridge 100 preferably comprises an in particular at least substantially planar, flat, plate-shaped and/or card-like main body or support 101, the main body or support 101 in particular being made of and/or injection-molded from plastics material, particularly preferably polypropylene.

The cartridge 100 preferably comprises at least one film or cover 102 for covering the main body 101 and/or cavities and/or channels formed therein at least in part, in particular on the front, and/or for forming valves or the like, as shown by dashed lines in FIG. 2.

The analysis system 1 or cartridge 100 or the main body 101 thereof, in particular together with the cover 102, preferably forms and/or comprises a fluidic system 103, referred to in the following as the fluid system 103.

The cartridge 100, the main body 101 and/or the fluid system 103 are preferably at least substantially vertically oriented in the operating position and/or during the test, in particular in the analysis device 200, as shown schematically in FIG. 1. In particular, the main plane or surface extension of the cartridge 100 thus extends at least substantially vertically in the operating position.

The cartridge 100 and/or the fluid system 103 preferably comprises a plurality of cavities, in particular at least one receiving cavity 104, at least one metering cavity 105, at least one intermediate cavity 106A-G, at least one mixing cavity 107, at least one storage cavity 108, at least one reaction cavity 109A-C, at least one intermediate temperature-control cavity 110 and/or at least one collection cavity 111, as shown in FIG. 1 and FIG. 2.

The cartridge 100 and/or the fluid system 103 also preferably comprises at least one pump apparatus 112 and/or at least one sensor arrangement or sensor apparatus 113.

Some, most or all of the cavities are preferably formed by chambers and/or channels or other depressions in the cartridge 100 and/or the main body 101, and particularly preferably are covered or closed by the cover 102. However, other structural solutions are also possible.

In the example shown, the cartridge 100 or the fluid system 103 preferably comprises two metering cavities 105, a plurality of intermediate cavities 106A to 106G, a plurality of storage cavities 108A to 108E and/or a plurality of reaction cavities 109A-C, which can preferably be loaded separately from one another, in particular a first reaction cavity 109A, a second reaction cavity 109B and an optional third reaction cavity 109C, as can be seen in FIG. 2.

The reaction cavity/cavities 109A-C is/are used in particular to carry out an amplification reaction, in particular PCR, or several, preferably different, amplification reactions, in particular PCRs. It is preferable to carry out several, preferably different, PCRs, i.e., PCRs having different primer combinations or primer pairs, in parallel and/or independently and/or in different reaction cavities 109A-C.

To carry out the nucleic-acid assay, preferably nucleic-acid sequences, as analytes A of the sample P, are amplified in the reaction cavity/cavities 109A-C by means of an amplification reaction, in particular in order to produce amplification products for the subsequent detection in the sensor arrangement or sensor apparatus 113.

Within the meaning of the present invention, amplification reactions are in particular molecular-biological reactions in which an analyte A, in particular a nucleic-acid sequence, is amplified/copied and/or in which amplification products, in particular nucleic-acid products, of an analyte A are produced. Particularly preferably, PCRs are amplification reactions within the meaning of the present invention.

"PCR" stands for polymerase chain reaction and is a molecular-biological method by means of which certain analytes A, in particular portions of RNA or RNA sequences or DNA or DNA sequences, of a sample P are amplified, preferably in several cycles, using polymerases or enzymes, in particular in order to then test and/or detect the amplification products or nucleic-acid products. If RNA is intended to be tested and/or amplified, before the PCR is carried out, a cDNA is produced starting from the RNA, in particular using reverse transcriptase. The cDNA is used as a template for the subsequent PCR.

Preferably, during a PCR, a sample P is first denatured by the addition of heat in order to separate the strands of DNA or cDNA. Preferably, primers or nucleotides are then deposited on the separated single strands of DNA or cDNA, and a desired DNA or cDNA sequence is replicated by means of polymerase and/or the missing strand is replaced by means of polymerase. This process is preferably repeated in a plurality of cycles until the desired quantity of the DNA or cDNA sequence is available.

For the PCR, marker primers are preferably used, i.e., primers which (additionally) produce a marker or a label, in particular biotin, on the amplified analyte A or amplification product. This allows or facilitates detection. Preferably, the primers used are biotinylated and/or comprise or form in particular covalently bonded biotin as the label.

The amplification products and/or other portions of the sample P produced in the one or more reaction cavities 109A-C can be conducted or fed to the connected sensor arrangement or sensor apparatus 113, in particular by means of the pump apparatus 112.

The sensor apparatus 113 is used in particular for detecting, particularly preferably qualitatively and/or quantitatively determining, the analyte A or analytes A of the sample P, in this case particularly preferably the nucleic-acid sequences and/or proteins as the analytes A. Alternatively or additionally, however, other values may also be collected or determined.

As already explained at the outset, in particular nucleic-acid sequences, preferably DNA sequences and/or RNA sequences, and/or proteins, in particular antigens and/or antibodies, are preferably qualitatively and/or quantitatively determined as analytes A of the sample P. In the following, however, a distinction is not made between nucleic-acid sequences and proteins, or between the nucleic-acid assay for detecting nucleic-acid sequences and the protein assay for detecting proteins.

In particular, the pump apparatus 112 comprises or forms a tube-like or bead-like raised portion, in particular by means of the film or cover 102, particularly preferably on the back of the cartridge 100, as shown schematically in FIG. 1.

The cartridge 100, the main body 101 and/or the fluid system 103 preferably comprise a plurality of channels 114 and/or valves 115A, 115B, as shown in FIG. 2.

By means of the channels 114 and/or valves 115A, 115B, the cavities 104 to 111, the pump apparatus 112 and/or the sensor arrangement and/or sensor apparatus 113 can be temporarily and/or permanently fluidically interconnected and/or fluidically separated from one another, as required and/or optionally or selectively, in particular such that they are controlled by the analysis system 1 or the analysis device 200.

The cavities 104 to 111 are preferably each fluidically linked or interconnected by a plurality of channels 114. Particularly preferably, each cavity is linked or connected by at least two associated channels 114, in order to make it possible for fluid to fill, flow through and/or drain from the respective cavities as required.

The fluid transport or the fluid system 103 is preferably not based on capillary forces, or is not exclusively based on said forces, but in particular is essentially based on the effects of gravity and/or pumping forces and/or compressive forces and/or suction forces that arise, which are particularly preferably generated by the pump or pump apparatus 112. In this case, the flows of fluid or the fluid transport and the metering are controlled by accordingly opening and closing the valves 115A, 115B and/or by accordingly operating the pump or pump apparatus 112, in particular by means of a pump drive 202 of the analysis device 200.

Preferably, each of the cavities 104 to 110 has an inlet at the top and an outlet at the bottom in the operating position. Therefore, if required, only liquid from the respective cavities can be removed via the outlet.

In the operating position, the liquids from the respective cavities are preferably removed, in particular drawn out, via the outlet that is at the bottom in each case, it preferably being possible for gas or air to flow and/or be pumped into the respective cavities via the inlet that is in particular at the top. In particular, relevant vacuums in the cavities can thus be prevented or at least minimized when conveying the liquids.

In particular, the cavities, particularly preferably the storage cavity/cavities 108, the mixing cavity 107 and/or the receiving cavity 104, are each dimensioned and/or oriented in the normal operating position such that, when said cavities are filled with liquid, bubbles of gas or air that may potentially form rise upwards in the operating position, such that the liquid collects above the outlet without bubbles. However, other solutions are also possible here.

The receiving cavity 104 preferably comprises a connection 104A for introducing the sample P. In particular, the sample P may for example be introduced into the receiving cavity 104 and/or cartridge 100 via the connection 104A by means of a pipette, syringe or other instrument.

The receiving cavity 104 preferably comprises an inlet 104B, an outlet 104C and an optional intermediate connection 104D, it preferably being possible for the sample P or a portion thereof to be removed and/or conveyed further via the outlet 104C and/or the optional intermediate connection 104D. Gas, air or another fluid can flow in and/or be pumped in via the inlet 104B, as already explained.

Preferably, the sample P or a portion thereof can be removed, optionally and/or depending on the assay to be carried out, via the outlet 104C or the optional intermediate connection 104D of the receiving cavity 104. In particular, a supernatant of the sample P, such as blood plasma or blood serum, can be conducted away or removed via the optional intermediate connection 104D, in particular for carrying out the protein assay.

Preferably, at least one valve 115A, 115B is assigned to each cavity, the pump apparatus 112 and/or the sensor apparatus 113 and/or is arranged upstream of the respective inlets and/or downstream of the respective outlets.

Preferably, the cavities 104 to 111 or sequences of cavities 104 to 111, through which fluid flows in series or in succession for example, can be selectively released and/or fluid can selectively flow there-through by the assigned valves 115A, 115B being actuated, and/or said cavities can be fluidically connected to the fluid system 103 and/or to other cavities.

In particular, the valves 115A, 115E are formed by the main body 101 and the film or cover 102 and/or are formed in another manner, for example, by additional layers, depressions or the like.

Particularly preferably, one or more valves 115A are provided which are preferably tightly closed initially or in the storage state, particularly preferably in order to seal liquids or liquid reagents F, located in the storage cavities 108, and/or the fluid system 103 from the open receiving cavity 104 in a storage-stable manner.

Preferably, an initially closed valve 115A is arranged upstream and downstream of each storage cavity 108. Said valves are preferably only opened, in particular automatically, when the cartridge 100 is actually being used and/or while inserting the cartridge 100 into the analysis device 200 and/or for carrying out the assay.

A plurality of valves 115A, in particular three valves in this case, are preferably assigned to the receiving cavity 104, in particular if the intermediate connection 104D is provided in addition to the inlet 104B and the outlet 104C. Depending on the use, in addition to the valve 115A on the inlet 104B, then preferably only the valve 115A either at the outlet 104C or at the intermediate connection 104D is opened.

The valves 115A assigned to the receiving cavity 104 seal the fluid system 103 and/or the cartridge 100 in particular fluidically and/or in a gas-tight manner until the sample P is inserted and the receiving cavity 104 or a connection 104A of the receiving cavity 104 is closed.

As an alternative or in addition to the valves 115A (which are initially closed), one or more valves 115B are preferably provided which are not closed in a storage-stable manner and/or which are open initially and/or which can be closed by actuation. These valves are used in particular to control the flows of fluid during the test.

The cartridge 100 is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 µl, in particular less than 600 µl or 300 µl, more particularly preferably less than 200 µl or 100 µl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as shown in the schematic view according to FIG. 2 by reference signs F1 to F5 and S1 to S10.

Furthermore, other liquids F, in particular in the form of a wash buffer, solvent for dry reagents S and/or a substrate, for example in order to form detection molecules and/or a redox system, are also preferably required for the test, the detection process and/or for other purposes, and are in particular provided in the cartridge 100, i.e., are likewise introduced before use, in particular before delivery. At some points in the following, a distinction is not made between liquid reagents and other liquids, and therefore the respective explanations are accordingly also mutually applicable.

The analysis system 1 or the cartridge 100 preferably contains all the reagents and liquids required for pretreating the sample P and/or for carrying out the test or assay, in particular for carrying out one or more amplification reactions or PCRs, and therefore, particularly preferably, it is only necessary to receive the optionally pretreated sample P.

The cartridge 100 or the fluid system 103 preferably comprises a bypass 114A that can optionally be used, in order for it to be possible, if necessary, to conduct or convey the sample P or components thereof past the reaction cavities 109A-C and/or, by bypassing the optional intermediate temperature-control cavity 110, also directly to the sensor apparatus 113.

The cartridge 100, the fluid system 103 and/or the channels 114 preferably comprise sensor portions 116 or other apparatus for detecting liquid fronts and/or flows of fluid.

It is noted that various components, such as the channels 114, the valves 115A, 115B, in particular the valves 115A that are initially closed and the valves 115B that are initially open, and the sensor portions 116 in FIG. 2 are, for reasons of clarity, only labelled in some cases, but the same symbols are used in FIG. 2 for each of these components.

The collection cavity 111 is preferably used for receiving excess or used reagents and liquids and volumes of the sample, and/or for providing gas or air in order to empty individual cavities and/or channels.

In particular, the collection cavity 111 can optionally be connected to individual cavities and channels or other apparatus fluidically in order to remove reagents and liquids from said cavities, channels or other apparatus and/or to replace said reagents and liquids with gas or air. The collection cavity 111 is preferably given appropriate large dimensions.

Once the sample P has been introduced into the receiving cavity 104 and the connection 104A has been closed, the cartridge 100 can be inserted into and/or received in the proposed analysis device 200 in order to test the sample P, as shown in FIG. 1. Alternatively, the sample P could also be fed in later.

FIG. 1 shows the analysis system 1 in a ready-to-use state for carrying out a test or assay on the sample P received in the cartridge 100, and/or in the operating position. In this state, the cartridge 100 is therefore linked to, received by and/or inserted into the analysis device 200.

In the following, some features and aspects of the analysis device 200 are first explained in greater detail, in particular on the basis of FIG. 1. The features and aspects relating to said device are preferably also directly features and aspects of the proposed analysis system 1, in particular even without any further explicit explanation.

The analysis system 1 or analysis device 200 preferably comprises a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed or sealed fluidic or hydraulic system 103 for the sample P and the reagents and other liquids. In this way, the analysis device 200 does not come into direct contact with the sample P and can in particular be reused for another test without being disinfected and/or cleaned first.

It is however provided that the analysis device 200 can be connected or coupled mechanically, electrically, thermally and/or pneumatically to the cartridge 100.

In particular, the analysis device 200 is designed to have a mechanical effect, in particular for actuating the pump apparatus 112 and/or the valves 115A, 115B, and/or to have a thermal effect, in particular for temperature-controlling the reaction cavity/cavities 109A-C and/or the intermediate temperature-control cavity 110.

In addition, the analysis device 200 can preferably be pneumatically connected to the cartridge 100, in particular in order to actuate individual apparatus, and/or can be electrically connected to the cartridge 100, in particular in order to collect and/or transmit measured values or measurement results 713, for example from the sensor apparatus 113 and/or sensor portions 116.

The analysis system 1 or analysis device 200 preferably comprises a pump drive 202, the pump drive 202 in particular being designed for mechanically actuating the pump apparatus 112.

Preferably, a head of the pump drive 202 can be rotated in order to rotationally axially depress the preferably bead-like raised portion of the pump apparatus 112. Particularly preferably, the pump drive 202 and pump apparatus 112 together form a pump, in particular in the manner of a hose pump or peristaltic pump and/or a metering pump, for the fluid system 103 and/or the cartridge 100.

Particularly preferably, the pump is constructed as described in German Patent DE 10 2011 015 184 B4 and corresponding U.S. Pat. No. 8,950,424. However, other structural solutions are also possible.

Preferably, the capacity and/or discharge rate of the pump can be controlled and/or the conveying direction of the pump and/or pump drive 202 can be switched. Preferably, fluid can thus be pumped forwards or backwards as desired.

The analysis system 1 or analysis device 200 preferably comprises a connection apparatus 203 for in particular electrically and/or thermally connecting the cartridge 100 and/or the sensor arrangement or sensor apparatus 113.

As shown in FIG. 1, the connection apparatus 203 preferably comprises a plurality of electrical contact elements 203A, the cartridge 100, in particular the sensor arrangement or sensor apparatus 113, preferably being electrically connected or connectable to the analysis device 200 by the contact elements 203A.

The analysis system 1 or analysis device 200 preferably comprises one or more temperature-control apparatus for temperature-controlling the cartridge 100 and/or having a thermal effect on the cartridge 100, in particular for heating and/or cooling, the temperature-control apparatus (each) preferably comprising or being formed by a heating resistor or a Peltier element.

Individual temperature-control apparatus, some of these apparatus or all of these apparatus can preferably be positioned against or abutted on the cartridge 100, the main body 101, the cover 102, the sensor arrangement, sensor apparatus 113 and/or individual cavities and/or can be thermally coupled thereto and/or can be integrated therein and/or in particular can be operated or controlled electrically by the analysis device 200. In the example shown, in particular the temperature-control apparatus 204A-C are provided.

Preferably, the temperature-control apparatus, referred to in the following as the reaction temperature-control apparatus 204A, is assigned to one of the reaction cavities 109A-C or to a plurality of reaction cavities 109A-C, in particular in order for it to be possible to carry out one or more amplification reactions therein.

The reaction cavities 109A-C are preferably temperature-controlled simultaneously and/or uniformly, in particular by means of one common reaction temperature-control apparatus 204A or two reaction temperature-control apparatus 204A.

More particularly, preferably, the reaction cavity/cavities 109A-C can be temperature-controlled from two different sides and/or by means of two or the reaction temperature-control apparatus 204A that are preferably arranged on opposite sides.

Alternatively, each reaction cavity 109A-C can be temperature-controlled independently and/or individually.

The temperature-control apparatus, referred to in the following as the intermediate temperature-control apparatus 204B, is preferably assigned to the intermediate temperature-control cavity 110 and/or is designed to (actively) temperature-control or heat the intermediate temperature-control cavity 110 and/or a fluid located therein, in particular the amplification products, preferably to a preheat temperature.

The intermediate temperature-control cavity 110 and/or intermediate temperature-control apparatus 204B is preferably arranged upstream of or (immediately) before the sensor arrangement or sensor apparatus 113, in particular in order for it to be possible to temperature-control or preheat, in a desired manner, fluids to be fed to the sensor arrangement or sensor apparatus 113, in particular analytes A and/or amplification products, particularly preferably immediately before said fluids are fed.

Particularly preferably, the intermediate temperature-control cavity 110 or intermediate temperature-control apparatus 204B is designed or provided to denature the sample P or analytes A and/or the amplification products produced, and/or to divide any double-stranded analytes A or amplification products into single strands and/or to counteract premature bonding or hybridizing of the amplification products, in particular by the addition of heat.

Preferably, the analysis system 1, analysis device 200 and/or the cartridge 100 and/or one or each temperature-control apparatus comprise/comprises a temperature detector and/or temperature sensor (not shown), in particular in order to make it possible to control and/or feedback control temperature.

One or more temperature sensors may for example be assigned to the sensor portions 116 and/or to individual channel portions or cavities, i.e., may be thermally coupled thereto.

The temperature-control apparatus 204C, referred to in the following as the sensor temperature-control apparatus 204C, is in particular assigned to the sensor apparatus 113 and/or is designed to (actively) temperature-control or heat fluids located in or on the sensor arrangement or sensor apparatus 113, in particular analytes A and/or amplification products, reagents or the like, in a desired manner, preferably to a hybridization temperature.

The sensor temperature-control apparatus 204C is preferably planar and/or has a contact surface which is preferably rectangular and/or corresponds to the dimensions of the sensor arrangement or sensor apparatus 113, the contact surface allowing for heat transfer between the sensor temperature-control apparatus 204C and the sensor apparatus 113.

Preferably, the analysis device 200 comprises the sensor temperature-control apparatus 204C. However, other structural solutions are also possible in which the sensor temperature-control apparatus 204C is integrated in the cartridge 100, in particular the sensor arrangement or sensor apparatus 113.

Particularly preferably, the connection apparatus 203 comprises the sensor temperature-control apparatus 204C, and/or the connection apparatus 203 together with the sensor temperature-control apparatus 204C can be linked to, in particular pressed against, the cartridge 100, in particular the sensor arrangement or sensor apparatus 113.

More particularly preferably, the connection apparatus 203 and the sensor temperature-control apparatus 204C (together) can be moved towards and/or relative to the cartridge 100, in particular the sensor arrangement or sensor apparatus 113, and/or can be positioned against said cartridge, preferably in order to both electrically and thermally couple the analysis device 200 to the cartridge 100, in particular the sensor arrangement or sensor apparatus 113 or the support thereof.

Preferably, the sensor temperature-control apparatus 204C is arranged centrally on the connection apparatus 203 or a support thereof and/or is arranged between the contact elements 203A.

In particular, the contact elements 203A are arranged in an edge region of the connection apparatus 203 or a support thereof or are arranged around the sensor temperature-control apparatus 204C, preferably such that the connection apparatus 203 is connected or connectable to the sensor apparatus 113 thermally in the center and electrically on the outside or in the edge region. However, other solutions are also possible here.

The analysis system 1 or analysis device 200 preferably comprises one or more valve actuators 205A, B for actuating the valves 115A, 115B. Particularly preferably, different (types or groups of) valve actuators 205A and 205B are provided which are assigned to the different (types or groups of) valves 115A and 115B for actuating each of said valves, respectively.

The analysis system 1 or analysis device 200 preferably comprises a control apparatus 207 for controlling the sequence of a test or assay and/or for collecting, evaluating and/or outputting or providing measured values or measurement results 713, in particular from the sensor apparatus 113, and/or from test results and/or other data or values.

The control apparatus 207 preferably comprises an internal clock or time base by means of which the sequence of the test is or can be controlled and/or by means of which test steps that follow temporally one another or that extend over time are controlled or can be controlled by the control apparatus 207.

The control apparatus 207 preferably controls or is designed to control actuators of the analysis device 200 for acting on the cartridge 100 in order to carry out the test. The actuators are in particular the pump drive 202, the temperature-control apparatus and/or the valve actuators 205A, B.

The analysis system 1 or analysis device 200 preferably comprises one or more sensors 206A-H. In particular, fluid sensors 206A are designed or provided to detect liquid fronts and/or flows of fluid in the fluid system 103. Particularly preferably, the fluid sensors 206A are designed to measure or detect, for example optically and/or capacitively, a liquid front and/or the presence, the speed, the mass flow rate/volume flow rate, the temperature and/or another value of a fluid in a channel and/or a cavity, in particular in a respectively assigned sensor portion 116, which is in particular formed by a planar and/or widened channel portion of the fluid system 103.

The fluid sensor 206A preferably measures a fluid entering or leaving the sensor portion 116 and/or a content change or fluid change in the sensor portion 116, and in the process generates a measurement result 706A that corresponds to the fluid entering, the fluid leaving, the content change and/or the fluid change in the sensor portion 116. This measurement result 706A from the fluid sensor 206A can be retrieved by the control apparatus 207 and/or transmitted to the control apparatus 207. The control apparatus 207 controls or is designed to control the test and/or the actuators, preferably using or taking into account the measurement result 706A from the fluid sensor 206A. In particular, when a content change, an entering fluid, a leaving fluid and/or a fluid change is detected in the sensor portion 116, in particular when a liquid front is detected, the control apparatus 207 influences a program sequence. In this case, for example a check can be carried out or a subsequent step of the test can be controlled, in particular by activating the actuators in a particular and/or differing manner.

Particularly preferably, the sensor portions 116 are each oriented and/or incorporated in the fluid system 103 and/or fluid flows against or through the sensor portions 116 such that, in the operating position of the cartridge 100, fluid flows through the sensor portions 116 in the vertical direction and/or from the bottom to the top, or vice versa, in particular in order to make it possible or easier to accurately detect liquid.

Alternatively, or additionally, the analysis device 200 preferably comprises one or more (different, other and/or further) sensors 206B.

Preferably, the other sensor 206B is or comprises a pressure sensor for determining the (relative) air pressure. The other sensor 206B can generate a measurement result 706B, which corresponds in particular to the air pressure. This measurement result 706B can be retrieved by the control apparatus 207 and/or transmitted to the control apparatus 207. The control apparatus 207 controls or is designed to control the test and/or the actuators, preferably using or taking into account the measurement result 706B from the other sensor 206B.

Alternatively or additionally, one or more temperature sensors 206C are provided for detecting the internal temperature and/or the temperature in the interior space 212A of the analysis device 200, in particular the temperature of an atmosphere in the interior space 212A. Alternatively or additionally, one or more temperature sensors 206C are provided for detecting the ambient temperature and/or the temperature of an atmosphere surrounding the analysis device 200 and/or the temperature of one or more of the temperature apparatus.

The temperature sensor 206C preferably measures a temperature, in particular of the interior space 212A of the analysis device 200, and in the process generates a measurement result 706C that corresponds to the temperature, in particular of the interior space 212A and/or atmosphere of or parts of the interior space 212A. This measurement result 706C from the temperature sensor 206C can be retrieved by the control apparatus 207 and/or transmitted to the control apparatus 207. The control apparatus 207 controls or is designed to control the test and/or the actuators, preferably using or taking into account the measurement result 706C from the temperature sensor 206C.

The analysis device 200 preferably comprises a tilt sensor 206D for detecting the inclination and/or orientation of the analysis device 200 and/or of the cartridge 100. The tilt sensor 206D is in particular designed and set up to determine the inclination of the analysis device 200 and/or of the cartridge 100 that differs from that in an operating position.

The tilt sensor 206D preferably measures the inclination, and in the process generates a measurement result 706D that corresponds to the inclination of the analysis device 200 and/or of the cartridge 100. This measurement result 706D from the tilt sensor 206D can be retrieved by the control apparatus 207 and/or transmitted to the control apparatus 207. The control apparatus 207 controls or is designed to control the test and/or the actuators, preferably using or taking into account the measurement result 706D from the tilt sensor 206D. In particular, if the inclination is too great, the test is prevented, blocked or interrupted, and/or an error is identified, processed, transmitted and/or signaled.

The analysis device 200 may comprise an acceleration sensor 206E. The acceleration sensor 206E is preferably designed to determine an acceleration of the analysis device 200, in particular an acceleration in the vertical and/or horizontal direction with respect to the operating position.

The acceleration sensor 206E preferably measures the acceleration, and in the process generates a measurement result 706E that corresponds to the acceleration of the analysis device 200 and/or of the cartridge 100. This measurement result 706E from the acceleration sensor 206E can be retrieved by the control apparatus 207 and/or transmitted to the control apparatus 207. The control apparatus 207 controls or is designed to control the test and/or the actuators, preferably using or taking into account the measurement result 706E from the acceleration sensor 206E. In particular, if the acceleration is too great, the test is prevented, blocked or interrupted, and/or an error is identified, processed, transmitted and/or signaled.

The analysis device 200 may comprise a humidity sensor 206F for determining the (relative) atmospheric humidity and/or the dew point of the atmosphere inside or in the interior space 212A and/or outside the analysis device 200.

The humidity sensor 206F preferably measures the (relative) atmospheric humidity and/or the dew point, and in the process generates a measurement result 706F that corresponds to the (relative) atmospheric humidity and/or the dew point of the atmosphere in the analysis device 200 and/or the surroundings of the analysis device 200. This measurement result 706F from the humidity sensor 206F can be retrieved by the control apparatus 207 and/or transmitted to the control apparatus 207. The control apparatus 207 controls or is designed to control the test and/or the actuators, preferably using or taking into account the measurement result 706F from the humidity sensor 206F. In particular, if the (relative) atmospheric humidity is too high and/or if the dew point is approached or reached, the test is prevented, blocked or interrupted, and/or an error is identified, processed, transmitted and/or signaled.

The analysis device 200 may comprise a position sensor 206G for determining the position or location, for example by means of a GPS sensor. The position sensor 206G is preferably designed to determine the location of the analysis device 200 in space, in particular on the Earth's surface, and/or to output the geographical position, the location and/or the coordinates of the analysis device 200.

The position sensor 206G preferably measures the position, in particular the geographical position, of the analysis device 200, and in the process generates a measurement result 706G that corresponds to the position or geographical position. This measurement result 706G from the position sensor 206G can be retrieved by the control apparatus 207 and/or transmitted to the control apparatus 207. The control apparatus 207 controls or is designed to control the test and/or the actuators, preferably using or taking into account the measurement result 706G from the position sensor 206G.

The analysis device 200 may comprise a cartridge sensor 206H for determining or checking the position or alignment of the cartridge 100 in or with respect to the analysis device 200. In particular, the cartridge sensor 206H is designed to detect an incorrect position of the cartridge 100 in the analysis device 200. Alternatively, or additionally, the cartridge sensor 206H is designed to detect and/or verify the correct and/or operating position of the cartridge 100 in the analysis device 200.

The cartridge sensor 206H preferably measures the position of the cartridge 100 in the analysis device 200, and in the process generates a measurement result 706H that corresponds to the position or alignment of the cartridge 100 in the analysis device 200. This measurement result 706H from the cartridge sensor 206H can be retrieved by the control apparatus 207 and/or transmitted to the control apparatus 207. The control apparatus 207 controls or is designed to control the test and/or the actuators, preferably using or taking into account the measurement result 706H from the cartridge sensor 206H. In particular, if the cartridge 100 is incorrectly positioned in the analysis device 200, the test is prevented or blocked and/or the cartridge 100 is automatically ejected from the analysis device 200 or the like. Alternatively, or additionally, the test is enabled if it is detected that the cartridge 100 is in the correct operating position in the analysis device 200.

The control apparatus 207 preferably controls or feedback controls the pump drive 202, the temperature-control apparatus 204 and/or the valve actuators 205, in particular taking into account or depending on the desired test and/or measured values from the sensor arrangement or sensor apparatus 113 and/or sensors 206A-H.

The flows of fluid are controlled in particular by accordingly activating the pump or pump apparatus 112 and actuating the valves 115A, 115B.

Particularly preferably, the pump drive 202 comprises a stepper motor, or a drive calibrated in another way, such that desired metering can be achieved, at least in principle, by means of appropriate activation.

Additionally, or alternatively, the fluid sensors 206A are used to detect liquid fronts or flows of fluid, in particular in cooperation with the assigned sensor portions 116, in order to achieve the desired fluidic sequence and the desired metering by accordingly controlling the pump or pump apparatus 112 and accordingly activating the valves 115A, 115B.

Optionally, the analysis system 1 or analysis device 200 comprises an input apparatus 208, such as a keyboard, a touch screen or the like, and/or a display apparatus 209, such as a screen.

The analysis system 1 or analysis device 200 preferably comprises at least one interface 210, for example for controlling, for communicating and/or for outputting measured data or test results and/or for linking to other devices, such as a printer, an external power supply or the like. This may in particular be a wired or wireless interface 210.

The analysis system 1 or analysis device 200 preferably comprises a power supply 211, preferably a battery or an accumulator, which is in particular integrated and/or externally connected or connectable.

Preferably, an integrated accumulator is provided as a power supply 211 and can be (re)charged by an external charging device (not shown) via a connection 211A and/or is interchangeable.

The analysis system 1 or analysis device 200 preferably comprises a housing 212, all the components and/or some or all of the apparatus preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis system 1 or analysis device 200 is preferably portable or mobile. Particularly preferably, the analysis device 200 weighs less than 25 kg or 20 kg, particularly preferably less than 15 kg or 10 kg, in particular less than 9 kg or 6 kg.

The fluidic, in particular pneumatic, coupling between the cartridge 100 and the analysis device 200 will be explained in greater detail in the following, it being possible for the following aspects to be implemented independently from the preceding aspects.

As already explained, the analysis device 200 can preferably be pneumatically linked to the cartridge 100, in particular to the sensor arrangement or sensor apparatus 113 and/or to the pump apparatus 112.

Particularly preferably, the analysis device 200 is designed to supply the cartridge 100, in particular the sensor arrangement or sensor apparatus 113 and/or the pump apparatus 112, with a working medium, in particular gas or air.

Preferably, the working medium can be compressed and/or pressurized in the analysis device 200 or by means of the analysis device 200.

Preferably, the analysis device 200 comprises a pressurized gas supply 214 for this purpose, in particular a pressure generator or compressor, preferably in order to compress and/or pressurize the working medium.

The pressurized gas supply 214 is preferably integrated in the analysis device 200 or the housing 212 and/or can be controlled or feedback controlled by means of the control apparatus 207. The pressurized gas supply 214 can also, at least in part, be formed on or by the cartridge 100.

Preferably, the pressurized gas supply 214 is electrically operated or can be operated by electrical power. In particular, the pressurized gas supply 214 can be supplied with electrical power by means of the power supply 211.

The analysis device 200 or pressurized gas supply 214 is preferably designed to compress the working medium to a pressure of more than 100 kPa, particularly preferably more than 150 kPa or 250 kPa, in particular more than 300 kPa or 350 kPa, and/or of less than 1 MPa, particularly preferably less than 900 kPa or 800 kPa, in particular less than 700 kPa and/or to feed said medium to the cartridge 100 at said pressure.

Preferably, air can be drawn in, in particular from the surroundings, as the working medium by means of the analysis device 200 or pressurized gas supply 214. In particular, the analysis device 200 or pressurized gas supply 214 is designed to use the surroundings as a reservoir for the working medium or the air. However, other solutions are also possible here, in particular those in which the analysis device 200 or pressurized gas supply 214 comprises a preferably closed or delimited reservoir, such as a tank or container, comprising the working medium, and/or is connected or connectable thereto.

Preferably, the analysis device 200 or pressurized gas supply 214 comprises an inlet, the working medium in particular being able to be drawn in and/or conducted in the pressurized gas supply 214 via the inlet.

Preferably, the analysis device 200 or pressurized gas supply 214 comprises a filter, the filter preferably being integrated in the inlet and/or it preferably being possible for the working medium to be filtered by means of the filter and/or it preferably being possible for particles to be separated from the working medium by means of the filter.

The filter is preferably designed as a micro filter or as a fine particulate air filter. Preferably, particles having a particle diameter of more than 10 particularly preferably more than 8 µm or 9 µm, in particular more than 6 µm or 7 µm, more particularly preferably more than 4 µm or 5 µm, can be separated by means of the filter, the particle diameter preferably being the maximum or average diameter of the respective particles. This ensures that the channels or lines in the cartridge that convey the working medium do not become contaminated or clogged and/or that no undesired pressure loss occurs.

The analysis device 200 or pressurized gas supply 214 preferably comprises a connection element 214A, in particular in order to pneumatically connect the analysis device 200 and/or pressurized gas supply 214 to the cartridge 100.

Figure 3:
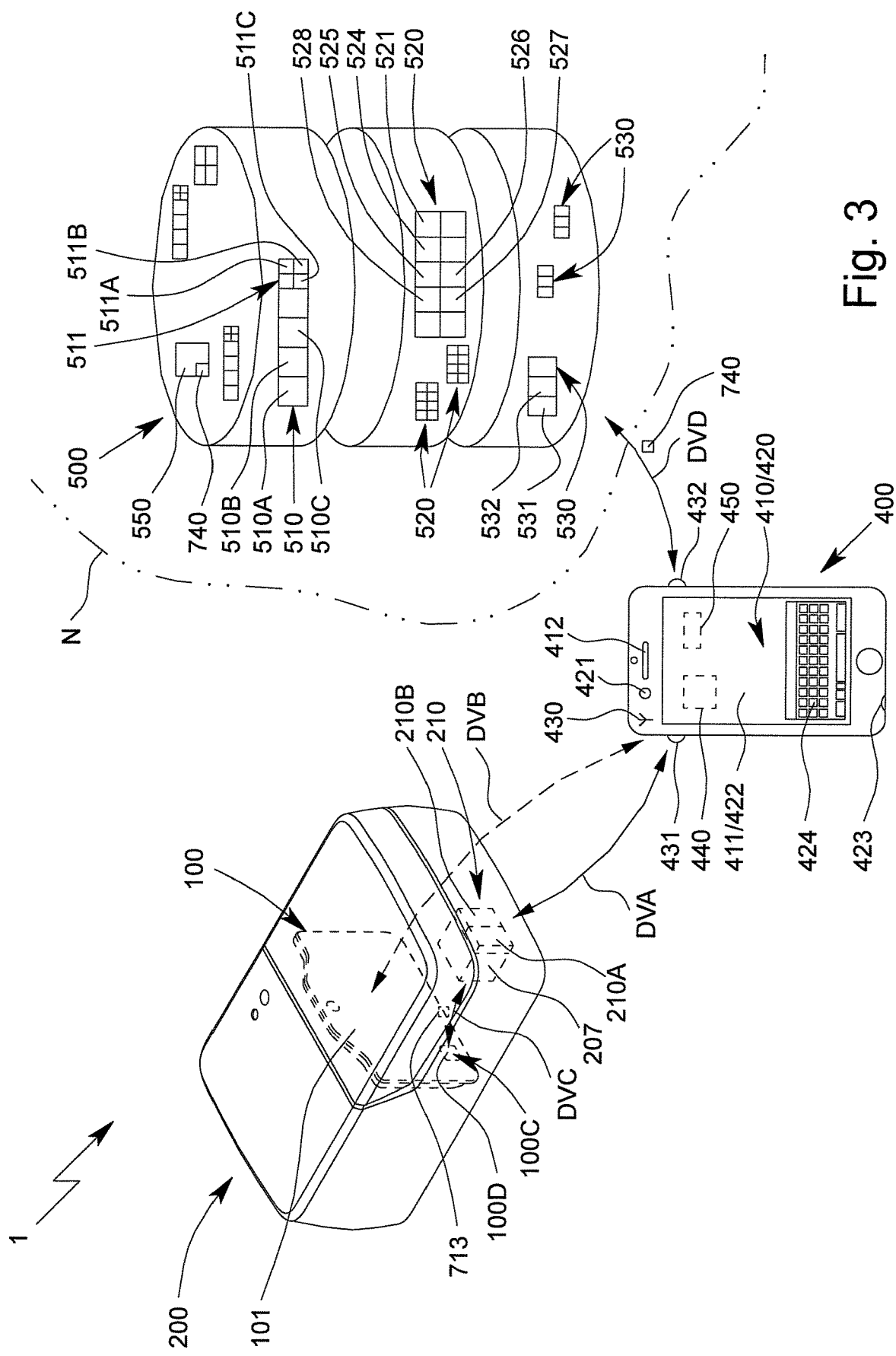
FIG. 3 is a schematic view of the analysis system.

FIG. 3 is a schematic view of the proposed analysis system 1 for testing an in particular biological sample P, comprising the analysis device 200 for receiving the cartridge 100 and subsequently carrying out the test using the received cartridge 100, and an operating instrument 400 for the analysis device 200.

The operating instrument 400 is preferably designed to control the analysis device 200. Alternatively, or additionally, the operating instrument 400 can receive or retrieve information, in particular (measurement) results such as measured values, from the analysis device 200. In particular, the operating instrument 400 is a mobile terminal device such as a smartphone, a tablet or the like.

The operating instrument 400 is preferably implemented or provided so as to be physically separated from the analysis device 200. The operating instrument 400 can preferably be separated and/or disconnected from the analysis device 200 physically and/or with respect to a data connection.

The operating instrument 400 can preferably be wirelessly connected to the analysis device 200. A data connection DVA can thus be established between the analysis device 200 and the operating instrument 400. However, the data connection DVA can in principle also be established in another manner, for example wired.

It is preferable for the operating instrument 400 to also be operational when separated or disconnected from the analysis device 200, in particular for carrying out evaluations or for other purposes. Alternatively, or additionally, the analysis device 200 is also operational when separated or disconnected from the operating instrument 400, in particular for continuing a test.

Particularly preferably, the operating instrument 400 comprises an interface 430 for establishing data connections DVA, DVB, DVD. The interface 430 and/or the operating instrument 400 in particular comprises what is referred to as an analysis device interface 431 that is designed to establish the preferably wireless data connection DVA to the analysis device 200. This can, for example, be a radio interface, WPAN interface, Bluetooth interface and/or a Bluetooth module or the like.

The interface 210 of the analysis device 200 preferably corresponds to the interface 430 and/or the analysis device interface 431 of the operating instrument 400, in particular such that the data connection DVA between the operating instrument 400 and the analysis device 200 can be established. The interface 210 of the analysis device 200 and the analysis device interface 431 preferably support the same data transmission method and/or radio transmission method or radio standard, in particular WLAN or WPAN methods such as Bluetooth, NFC, Zigbee or the like.

Particularly preferably, the interface 210 of the analysis device 200 and the analysis device interface 431 make possible or facilitate what is known as an ad-hoc connection. In this case, the data connection DVA is established preferably automatically when the devices, i.e., the operating instrument 400 and the analysis device 200, are within range of one another. In other words, the operating instrument 400 and the analysis device 200 each comprise a wireless data interface 430, 210, respectively, which are designed to jointly establish an ad-hoc data connection between the operating instrument 400 and the analysis device 200, preferably such that, when the operating instrument 400 and the analysis device 200 approach one another in space, the data connection DVA therebetween is automatically established and is preferably displayed by means of the operating instrument 400.

The data connection DVA is preferably a point-to-point connection. The data connection DVA connects the analysis device 200 to the operating instrument 400 preferably directly and/or without any interposed networks. It is possible for the operating instrument 400 to establish data connections DVA to different analysis devices 200 simultaneously or in succession. Alternatively, or additionally, it is possible for one analysis device 200 to establish data connections DVA to a plurality of operating instruments 400 simultaneously or in succession.

In order to control the test, it is preferable for precisely one data connection DVA to be provided between the analysis device 200 to be controlled and the operating instrument 400 controlling the analysis device 200, and/or for control information 510 to be received and/or accepted or to be acceptable and/or receivable and/or for measurement results 713 to be transmitted or to be transmittable only via precisely one data connection DVA between the analysis device 200 to be controlled and the operating instrument 400 controlling the analysis device 200.

The analysis device 200 preferably comprises a receiver 210A for, preferably wirelessly, receiving the control information 510 from the operating instrument 400. Preferably, the interface 210 comprises the receiver 210A, via which signals, in particular control information 510, are or can be received from the operating instrument 400.

Alternatively, or additionally, the analysis device 200 and/or the interface 210 comprises a transmitter 210B, via which data, in particular results such as measurement results 713 from the sensor apparatus 113, are or can be sent, particularly preferably to the operating instrument 400.

The interfaces 210, 431 preferably correspond to one another such that they support the same data transmission standard and/or radio standard, in particular Bluetooth, WLAN or the like. These interfaces are particularly preferably interfaces 210, 431 which make possible what is known as an ad-hoc connection, the data connection DVA preferably being established automatically when the devices, i.e., the operating instrument 400 and the analysis device 200, are within range of one another.

The analysis system 1 preferably further comprises a database 500 or the database 500 is assigned to the analysis system 1. The database 500 is preferably an external database 500 that is implemented or provided so as to be physically separated from the operating instrument 400 and/or from the analysis device 200. In principle, however, it is not impossible for the database 500 to be provided or implemented such that it can be directly linked, in particular to the operating instrument 400, or to be provided or implemented by the operating instrument 400.

The operating instrument 400 can access the database 500 via a data connection DVD. For this purpose, the operating instrument 400 and/or the interface 430 can comprise a database interface 432 by means of which the database 500 can be accessed, in particular via a network N. The network N may be the Internet or another data network. It is also preferable for the operating instrument 400 to be able to establish the data connection DVD to the database 500 via a wireless interface, in particular WLAN, WPAN, mobile communications or the like. However, in principle, other solutions are also possible here.

Particularly preferably, the operating instrument 400 comprises different interfaces 430 that are independent of one another for establishing data connections DVA, DVD to the analysis device 200 and to the database 500, the analysis device 200 (as a peripheral device of the operating instrument 400) being designed to communicate exclusively with or via the operating instrument 400.

The analysis system 1, in particular the database 500, preferably comprises control information 510 by means of which the analysis device 200 can be controlled in order to carry out a test.

The control information 510 preferably defines the actuation of the actuators of the analysis device 200 in a particular manner, such that the sample P is tested in the cartridge 100. In particular, actuators for carrying out the test can be or are controlled using the control information 510 such that said actuators act on the cartridge 100 and/or the sample P. These actuators are in particular the pump drive 202 and/or one or more temperature-control apparatus 204 and/or one or more valve actuators 205. The control information 510 preferably comprises parameters and/or instructions for carrying out one or more steps of the method for testing the sample P explained above.

Preferably, the analysis system 1 comprises calibration information 520 that can be stored in the database 500 and/or can be retrieved from the database 500. The calibration information 520 is preferably capable of influencing the test of the sample P, in particular depending on the specific cartridge 100, on a cartridge batch of the specific cartridge 100 and/or on the specific test.

The calibration information 520 is in particular default or basic settings, parameters and/or threshold values for sensors such as the sensor apparatus 113 of the cartridge 100, for one or more of the sensor(s) 206A-H of the analysis device 200 and/or for one or more of the actuators.

Calibration information 520 can be used in addition to control information 510 for carrying out the test, the calibration information 520 preferably influencing or specifying the control information 510. The calibration information 520 can be or can form the control information 510 or a part of the control information 510, even if this is not explicitly mentioned in the following.

The analysis device 200 can be calibrated and/or configured by calibration information 520 that can form part of the control information 510 or can be provided separately. For this purpose, the calibration information 520 can be determined, retrieved and/or transmitted to the analysis device 200 by means of the operating instrument 400.

In one example, fluid sensor calibration information 521 is provided which influences setting and/or evaluation of the fluid sensor 206A. The fluid sensor calibration information 521 is preferably dependent on the test to be carried out, the phase of the test and/or expected effects of a content change in a sensor portion 116 during the test sequence, and/or contains various specifications which are dependent thereon.

Alternatively, or additionally, tilt sensor calibration information 524 can be provided, preferably comprising one or more threshold values 525, in particular a start threshold value 526 for blocking the start of a test if said threshold value is exceeded, and/or an interruption threshold value 527 for interrupting the test and/or for processing errors if said threshold is exceeded.

Alternatively, or additionally, sensor arrangement calibration information 528 can be provided, by means of which properties of the sensor arrangement or sensor apparatus 113 are or can be set. In particular, it is provided that the sensor arrangement calibration information 528 is transmitted or can be transmitted to the sensor arrangement or sensor apparatus 113 by the analysis device 200, and that the sensor arrangement or sensor apparatus 113 carries out or is designed to carry out a measurement taking into account the sensor arrangement calibration information 528.

The proposed analysis system 1 preferably comprises evaluation information 530 which is stored in the database 500 and/or is retrievable or can be retrieved from the database 500. The evaluation information 530 is preferably designed to be able to interpret measurement results 713 that originate from the cartridge 100, in particular from the sensor apparatus 113.

The control information 510 and/or the evaluation information 530 particularly preferably comprises instructions, preferably in the form of an algorithm and/or for controlling a process on or using a processor or controller. The instructions preferably form a module that can be or is implemented by the analysis device 200 and/or the operating instrument 400, as a result of which the behavior of the analysis device 200 and/or the operating instrument 400 can be or is changed.

The instructions are in particular commands, machine code, pre-compiled source code or source code. The instructions preferably form a module-type software component, in particular a plugin. The instructions can be designed to form and/or to replace a module of the operating instrument 400 and/or of the analysis device 200. For this purpose, the control information 510 and/or the evaluation information 530 can comprise a (software) interface for coupling or implementation by the control apparatus 207 and/or an evaluation module 440 of the operating instrument 400.

The control information 510 particularly preferably comprises or forms a module of the control apparatus 207 that can be exchanged, preferably in terms of software. This module preferably contains instructions such as logic commands, loops and the like for controlling the test, in particular in the form of a computer program or computer program product to be executed by the analysis device 200 and/or the control apparatus 207. The control information 510 can be or form, in particular as a plugin, an exchangeable part of the control apparatus 207.

An evaluation module 440 is preferably formed by the operating instrument 400 or the operating instrument 400 comprises the evaluation module 440. By means of the evaluation module 440, measurement results 713 read out from the sensor apparatus 113 are evaluated preferably using the evaluation information 530 retrieved from the database 500 and/or the evaluation module 440 is designed for this purpose.

The evaluation information 530 particularly preferably comprises or forms a module of the evaluation apparatus 440 that can be exchanged, preferably in terms of software. This module preferably contains instructions such as logic commands, loops and the like for controlling the evaluation of measurement results 713, in particular in the form of a computer program or computer program product to be executed by the operating instrument 400 and/or the evaluation module 440. The evaluation information 530 can be or form, in particular as a plugin, an exchangeable part of the evaluation module 440. The computer program product preferably is a non-transitory computer-readable media.

Alternatively, or additionally, the instructions can comprise parameters for configuring the control apparatus 207 and/or the evaluation module 440. These parameters are preferably provided in addition to the instructions, for example for the analysis device 200 in the form of or comprising the calibration information 520. Alternatively, the control information 510 and/or evaluation information 530 can however also merely comprise parameters and/or other information for the control and/or evaluation.

The database 500 preferably comprises a results memory 550 in which results can be stored and/or saved.

Within the meaning of the present invention, the term "database" should preferably be understood in a broad sense and also incorporates multi-part databases in particular. Therefore, in principle, the database 500 can be provided in different physical units or at different locations and/or can be composed of a plurality of sub-databases.

The operating instrument 400 can preferably be separated and/or disconnected from the analysis device 200 with respect to a data connection and/or physically. For this purpose, the analysis device 200 can initially be connected to the operating instrument 400 by the data connection DVA being established.

In order to control the test and/or the analysis device 200, the operating instrument 400 can retrieve control information 510 from the database 500 and transmit said information to the analysis device 200 in unaltered or altered form.

The operating instrument 400 is preferably designed to evaluate measurement results 713 which can preferably be generated by the sensor apparatus 113 of the cartridge 100 while the sample P is being tested. For this purpose, it is provided that measurement results 713, which can originate from a sensor apparatus 113 of the cartridge 100 and/or which can be transmitted from the analysis device 200 to the operating instrument 400, are or can be evaluated in the operating instrument 400. For this purpose, the operating instrument 400 can retrieve or receive the evaluation information 530 from the database 500 and, using this evaluation information 530, evaluate the measurement results 713, in particular in the evaluation module 440 of the operating instrument 400.

The operating instrument 400 preferably comprises a memory 450. The memory 450 can be used to store, at least temporarily, control information 510, calibration information 520 and/or evaluation information 530, or the operating instrument 400 and the memory 450 can be designed for this purpose. Alternatively, or additionally, evaluation results 740, that have been or can be generated from the measurement results 713 by means of the operating instrument 400, can be stored in the memory 450.

In one example, the operating instrument 400 comprises an output apparatus 410, preferably an in particular touch-sensitive screen or display 411 and/or a speaker 412. Alternatively, or additionally, the operating instrument 400 comprises an input apparatus 420, in particular a camera 421, a touchpad 422, a microphone 423 and/or a keyboard 424.

The operating instrument 400 is preferably designed to display an operating interface or a user interface via the output apparatus 410, in particular the screen or display 411, or to provide in another way operating elements for controlling the test and/or the analysis device 200, and/or to output a status or other information relating to the test. Alternatively, or additionally, commands can be received via the input apparatus 420, by means of which the operating instrument 400 starts, configures and/or controls the test of the sample P in a manner corresponding to the commands.

Preferably, the transmission of commands and/or information to the analysis device 200 is triggered via the input apparatus 420 or can be triggered by the input apparatus 420.

In particular, transmission of the control information 510 from the operating instrument 400 to the analysis device 200 can be initiated or controlled via the input apparatus 420. Alternatively, or additionally, the analysis device 200 can be controlled in order to receive the cartridge 100 and/or to start the test, preferably using the control information 510 and/or a command received via the input apparatus 420. The operating instrument 400 is therefore preferably designed to transmit to the analysis device 200 control information 510 for receiving or ejecting the cartridge 100. In this case, a cartridge 100 can in particular be inserted only when the operating instrument 400 is connected to the analysis device 200, whereupon the operating instrument 400 can verify the cartridge 100 and can eject said cartridge or block a test if an error, such as incompatibility, is detected.

Alternatively, or additionally, the operating instrument 400 is designed to transmit control information 510 for starting the test to the analysis device 200. The test is thus preferably started only by a command originating from the operating instrument 400. The analysis device 200 itself preferably does not comprise a user interface for generating a start command or for causing the test to start. This task is preferably reserved for the operating instrument 400.

The cartridge 100 preferably comprises at least one cartridge identifier 100C which corresponds to the cartridge 100 and/or to a batch with which the cartridge 100 is associated.

The cartridge identifier 100C is in particular a piece of information that is specific to the relevant cartridge 100, is in particular unique and/or is designed to uniquely identify the cartridge 100, such as an identification code which is assigned to the relevant cartridge 100 and makes it possible for said cartridge to be identified in a preferably unique manner.

Alternatively, or additionally, the cartridge identifier 100C makes it possible to assign the cartridge 100 to a production cycle and/or to a batch of particular cartridges 100. A batch is preferably characterized in that cartridges 100 are produced in the same continuous production cycle and/or are produced having the same components, in particular having the same sensor apparatus 113 and/or the same reagents and the like. There is preferably a plurality of batches which can differ from one another with regard to production periods, batches of starting materials used and the like, for example.

The cartridge identifier 100C can be stored and/or saved in a memory means 100D of the cartridge 100. The memory means 100D can be a barcode 124, an NFC tag and/or a memory which is provided in the sensor apparatus 113, is connected to the sensor apparatus 113 or is assigned to the sensor apparatus 113, or another apparatus for storing code or the like.

The cartridge identifiers 100C are preferably assigned to the respective cartridges 100. In particular, the cartridge identifier 100C is formed by the cartridge 100, connected thereto and/or arranged thereon.

The analysis system 1 can comprise one or a plurality of cartridges 100 which can each preferably be distinguished from one another by means of at least one cartridge identifier 100C and/or which are assigned to a batch.

Another aspect of the present invention, which can also be implemented independently, relates to a cartridge 100 having at least two cartridge identifiers 100C that each correspond to the cartridge 100. The cartridge identifiers 100C can preferably be read out by different read-out methods, in particular optically, by radio, by a wired connection or the like.

The respective cartridges 100 can comprise two different memory means 100D having the same or corresponding cartridge identifiers 100C. The memory means 100D are preferably independent of one another and/or separated from one another physically. The memory means 100D can preferably be read out in different ways, in particular electronically and/or by an electronic connection on the one hand, and wirelessly, in particular optically and/or by radio on the other hand.

In the example shown, corresponding cartridge identifiers 100C are stored, saved or recorded both in a memory that can be read out electronically, in particular of the sensor apparatus 113, and in a memory that can be read out wirelessly, by radio or optically, in particular the barcode 124. This makes it possible for the cartridge identifier 100C or the cartridge identifiers 100C corresponding to the same cartridge 100 to be read out in different ways.

This advantageously makes it possible to retrieve control information 510, calibration information 520 and/or evaluation information 530 from the database 500 independently, disconnected or separately from the analysis device 200, preferably by optically reading out the cartridge identifier 100C from the cartridge 100. Alternatively or additionally, a memory means 100D of the cartridge 100 that can be read out electronically makes it possible for the cartridge identifier 100C to be read out without there being an optical connection to or visual contact with the cartridge 100, for example when said cartridge is inserted into the analysis device 200.

The at least two cartridge identifiers 100C can be the same or, in one aspect of the present invention, which can also be implemented independently, said cartridge identifiers 100C can be different. In particular, it is possible and preferable for a (first) cartridge identifier 100C to be individual or unique to the cartridge 100, i.e., designed to uniquely identify the cartridge 100. A (different or second) cartridge identifier 100C is preferably designed to assign the cartridge 100 to a batch of cartridges 100. The at least two cartridge identifiers 100C preferably correspond to one another. In particular, the cartridge identifier 100C corresponding to the batch and/or the batch can be identified using the cartridge identifier 100C that uniquely identifies the cartridge 100. Preferably, both cartridge identifiers 100C are read out and used, in particular in order to determine and/or retrieve control information 510 and/or evaluation information 530 on the one hand and in order to verify said information on the other hand.

The respective cartridges 100 are preferably identified at least twice or a cartridge identifier 100C is read out and used at least twice, namely preferably once directly by the operating instrument 400 in order to retrieve control information 510 and/or calibration information 520 and/or evaluation information 530 and a second time by means of or via the analysis device 200 in order to ensure that the test is carried out using control information 510, calibration information 520 and/or evaluation information 530 that corresponds to the cartridge 100 and/or in order to ensure and/or verify that the control information 510, calibration information 520 and/or evaluation information 530 corresponds to the cartridge 100.

FIG. 4 shows a schematic sequence of a preferred method for testing and/or evaluating by means of the proposed analysis system 1, in particular in a manner which is dependent on the individual cartridge 100. The following aspects and/or method steps can also be implemented and can be advantageous individually or in different combinations, the described order being preferred, but not obligatory, and it being possible for steps to be omitted or added or carried out independently.

As explained above, at least one cartridge identifier 100C corresponds to the (respective) cartridge 100. This cartridge identifier 100C is preferably stored in a memory means 100D, in particular the barcode 124 and/or a memory cell of the sensor apparatus 113, on the cartridge 100. However, in principle, other storage options are possible here or there is the option of providing other memory means 100D. For example, a memory means 100D assigned to the cartridge 100 can be arranged on the packaging of the cartridge 100 or can form part of said packaging.

Preferably, the cartridge 100, in particular the sensor apparatus 113, is electrically contacted by the analysis device 200. This is preferably achieved by one or more contact elements 203A, as shown in FIG. 1 by way of example.

If the cartridge identifier 100C is stored in the sensor apparatus 113 or is assigned thereto, said cartridge identifier 100C can be read out by the analysis device 200 via a data connection DVC between the cartridge 100 and the analysis device 200 that can be created by means of the contact elements 203A. This is symbolized by the arrow 601, which represents the data transmission from the cartridge 100 to the analysis device 200. The cartridge identifier 100C stored in the sensor apparatus 113 and/or assigned to the sensor apparatus 113 identifies the cartridge 100 preferably uniquely or on a one-to-one basis.

The cartridge identifier 100C read out from the cartridge 100 by the analysis device 200 can be transmitted to the operating instrument 400 via the data connection DVA between the analysis device 200 and the operating instrument 400, as indicated in FIG. 4 by the arrow 602, which represents the data transmission between the analysis device 200 and the operating instrument 400. In addition to the cartridge identifier 100C, a device identifier 200C can optionally also be transmitted from the analysis device 200 to the operating instrument 400. The device identifier 200C preferably corresponds to the specific analysis device 200 and/or makes it possible for the analysis device 200 to be identified.

In an alternative, which can also be carried out additionally, the cartridge identifier 100C is or can be determined directly by the operating instrument 400. Particularly preferably, this is achieved optically and/or using the camera 421 of the operating instrument 400, preferably by reading in a code, in particular the barcode 124. It is however also possible for the cartridge identifier 100C to be directly and/or wirelessly determined from the relevant cartridge 100 by the operating instrument 400 in some other way, for example by radio, in particular by reading out an RFID tag which is optionally assigned to the cartridge 100 or arranged on the cartridge 100, or an NFC memory apparatus or the like which is assigned to the cartridge 100, is arranged on the cartridge 100 or forms part of the cartridge 100 in some other way.

As a result, the cartridge identifier 100C is therefore particularly preferably transmitted to the operating instrument 400 either directly by the operating instrument 400 reading out the memory means 100D of the cartridge 100, or indirectly by data being correspondingly transferred via the analysis device 200, and the operating instrument 400 thereby receives or determines the cartridge identifier 100C.

In one aspect of the present invention, which can also be implemented independently, the operating instrument 400 receives or determines information, which is preferably cartridge-specific and/or cartridge-batch-specific, by means of the cartridge identifier 100C, or the operating instrument 400 is designed for this purpose.

The operating instrument 400 retrieves or is designed to retrieve, preferably automatically, the control information 510 for controlling the analysis device 200 in order to carry out the test supported by the cartridge 100 and/or analysis information 530 for evaluating measurement results 713 determined during the test, by reading out the cartridge identifier 100C of the cartridge 100 or after said cartridge identifier 100C has been read out.

In particular, it is provided that the operating instrument 400 receives or retrieves control information 510 on the basis of the cartridge identifier 100C, which information is specific to the cartridge 100, the batch thereof and/or specific for carrying out the test using the cartridge 100. Particularly preferably, the control information 510 is retrieved from the database 500 or can be retrieved from the database 500.

Preferably, the cartridge identifier 100C is transmitted to the database 500, as indicated in FIG. 4 by the arrow 603, which corresponds to the data transmission from the operating instrument 400 to the database 500.

The database 500 can send back control information 510 corresponding to the cartridge 100 and/or to the cartridge identifier 100C, i.e., transmit said information to the operating instrument 400, as indicated in FIG. 4 by the arrow 604, which represents the data transmission between the database 500 and the operating instrument 400.

Alternatively, or additionally, calibration information 520 and/or evaluation information 530 can also be transmitted to the operating instrument 400 in a corresponding manner from the database 500 to the operating instrument 400 or is or can be retrieved from the database 500 by the operating instrument 400.

In one variant, the information can also be retrieved without the cartridge identifier 100C being transmitted to the database 500. In a variant of this kind, control information 510, calibration information 520 and/or evaluation information 530 which is available to the operating instrument 400 and, for example, has been previously retrieved and/or temporarily stored in the operating instrument 400, can be identified by means of the operating instrument 400 on the basis of the cartridge identifier 100C and can be selected for subsequent use.

In another variant, which can be combined with the two previous methods for determining and/or retrieving the control information 510, calibration information 520 and/or evaluation information 530, the information is selected and/or retrieved in addition by using and/or transmitting a device identifier 200C for identifying the analysis device 200 and/or an operating instrument identifier 400C for identifying the operating instrument 400. This makes it possible for the control information 510, calibration information 520 and/or evaluation information 530 to be specific to or compatible with the analysis device 200 and/or the operating instrument 400 and for said information to be selected, transmitted, retrieved and/or sent back in a manner in which it is specific to or compatible with the analysis device 200 and/or the operating instrument 400.

Preferably, control information 510 is retrieved or determined that corresponds to both the cartridge 100 and the analysis device 200, particularly preferably to the combination of the cartridge 100 and the analysis device 200. As a result, the test can be carried out in a manner which is specific to both the cartridge 100 and the analysis device 200, and this contributes to making tests highly reproducible and reliable.

In one aspect of the present invention, which can also be implemented independently, the cartridge identifier 100C, which preferably corresponds only to the batch with which the cartridge 100 is associated, is first determined by the operating instrument 400, in particular is or can be read out from the cartridge 100 directly by the operating instrument 400.

Using the cartridge identifier 100C, the control information 510 and/or evaluation information 530 is retrieved, in particular by means of the operating instrument 400. The retrieved control information 510 and/or evaluation information 530 is preferably stored temporarily in the operating instrument 400.

The control information 510 is transmitted by the operating instrument 400 preferably to the analysis device 200 or the operating instrument 400 is designed for this purpose. This is indicated in FIG. 4 by the arrow 605, which corresponds to data transmission from the operating instrument 400 to the analysis device 200.

Optionally, calibration information 520 can also be transmitted from the operating instrument 400 to the analysis device 200. Alternatively, or additionally, the operating instrument 400 can modify the control information 510, in particular taking into account the calibration information 520. The control information 510 can however also already comprise or incorporate the calibration information 520. It is therefore not obligatory for the calibration information 520 to be transmitted to the analysis device 200.

Preferably, transmission only takes place if the cartridge 100, the control information 510, and the assignment, association and/or compatibility thereof have been verified. This ensures that the control information 510 to be transmitted corresponds to the cartridge 100 which is intended to be used to carry out the test. This is provided for in particular if the control information 510 and/or evaluation information 530 has been previously retrieved by the operating instrument 400 and/or stored temporarily in the operating instrument 400.

Verification is achieved particularly preferably by a/the cartridge identifier 100C. In particular, for verification, a cartridge identifier 100C different from the cartridge identifier for retrieving the control information 510 and/or evaluation information 530 is used, and/or a cartridge identifier 100C that is read out from another memory means 100D of the cartridge 100 is used.

The cartridge identifier 100D provided for verification is preferably read out by means of or via the analysis device 200 and/or transmitted to the operating instrument 400. This takes place if the cartridge 100 is in direct contact with the analysis device 200 for carrying out the test, i.e., if the cartridge 100 is in particular loaded or inserted into the analysis device 200. This ensures that the cartridge 100 which is intended to be used to carry out the test is determined. Verification by means of the cartridge identifier 100C of the cartridge 100 therefore makes it possible to ensure that the test is carried out using the control information 510 that corresponds to the cartridge 100.

Verification can be achieved by checking that the cartridge identifier 100D provided for verification is assigned to the control information 510 and/or by checking that the cartridge identifier 100C provided for verification is assigned to the cartridge identifier 100C used for determining the control information 510. In this respect, it can be checked whether the cartridge identifier 100C provided for verification corresponds to the batch of cartridges 100 to which the control information 510 corresponds. This can be achieved by an assignment, allocation or mapping, such as a table or database, and/or by verification means which are assigned to or form part of the control information 510. For this purpose, the control information 510 can comprise corresponding assignment means, for example information relating to cartridge identifier groups. Verification can be carried out by these assignment means.

Other retrieved information, in particular the evaluation information 530, can be verified in a corresponding manner.

The control information 510 can be received by the analysis device 200 and used for controlling the test. Alternatively, or additionally, the control information 510 can also be verified in the analysis device 200.

After the control information 510 has been transmitted, the test is started, preferably in a manner controlled by the operating instrument 400.

In FIG. 4, the testing process on the cartridge 100 by means of the analysis device 200 is indicated by the arrow 606.

According to one aspect of the present invention, which can also be implemented independently, the analysis device 200 is designed to carry out the test using the transmitted control information 510 and independently and/or separately and/or disconnected from the operating instrument 400 and/or the test is carried out independently and/or separately and/or disconnected from the operating instrument 400.

Particularly preferably, the test is carried out independently and/or separately from the operating instrument 400. For this purpose, the analysis device 200 is preferably designed to carry out or continue the test using the transmitted control information 510 and independently and/or separately and/or disconnected from the operating instrument 400 and/or when the data connection DVA is disconnected, terminated or broken.

This makes it possible for example to transmit the control information 510 to the analysis device 200 by means of the operating instrument 400, to start the test process, and to subsequently disconnect, terminate or break the data connection DVA between the analysis device 200 and the operating instrument 400, such that the analysis device 200 carries out or can carry out the test self-actingly, automatically and/or autonomously of and independently from the operating instrument 400. Therefore, while the test is underway, a user together with the operating instrument 400 can move away from the analysis device 200 and/or can use the operating instrument 400 for other purposes.

In order to carry out the test, the analysis device 200 preferably acts on the cartridge 100 such that the sample P is prepared, conveyed and/or analyzed inside the cartridge 100, or the analysis device 200 is designed for this purpose. Preferably, the test is or can be controlled by the control apparatus 207 of the analysis device 200.

In order to carry out the test, the analysis device 200 preferably receives the control information 510 and, preferably, the calibration information 520, particularly preferably via the operating instrument 400 in each case. For this purpose, the operating instrument 400 is preferably designed to transmit, and the analysis device 200 is designed to receive, the control information 510 and, preferably, the calibration information 520.

Using the control information 510, the control apparatus 207 controls apparatus and/or actuators of the analysis device 200 such that said apparatus and/or actuators act on the cartridge 100, or the control apparatus 207 is designed for this purpose.

The actuators are in particular the pump drive 202, the temperature-control apparatus 204 and/or the (valve) actuators 205. By means of the actuators, the sample P can be conveyed within the fluid system 103 of the cartridge 100 and/or the temperature of the sample P can be changed and/or the sample P can be mixed with reagents and/or prepared and/or fed to the sensor apparatus 113 in order to ultimately determine, by means of the sensor apparatus 113, measurement results 713 that correspond to the sample P.

The sample P is preferably conveyed inside the cartridge 100 to the sensor apparatus 113 in a manner specified by the control information 510 and/or the analysis device 200 is designed to do this, preferably together with the cartridge 100.

Valves 115A, 115E of the cartridge 100 are preferably opened or closed in a manner specified by the control information 510 and/or the analysis device 200 is designed to do this, preferably together with the cartridge 100.

One or more temperature-control apparatus 204 of the analysis device 200 are preferably controlled such that the sample P and/or sensor apparatus 113 are temperature-controlled in a manner specified by the control information 510 and/or the analysis device 200 is designed to do this, preferably together with the cartridge 100.

Control on the basis of the control information 510 and, preferably, of the calibration information 520 is preferably carried out, as explained in connection with FIGS. 1 and 2, in particular so as to carry out a nucleic-acid assay for detecting a nucleic-acid sequence and/or a protein assay for detecting a protein. The control information 510 is therefore preferably designed to, the control information 510 in particular comprising instructions and/or parameters, in order to carry out a nucleic-acid assay for detecting a nucleic-acid sequence and/or a protein assay for detecting a protein. However, other assays are also possible.

The control information 510 preferably comprises valve control information 510A for actuating one or more valve actuators 205 in order to open and/or close valves on the cartridge 100.

Alternatively, or additionally, the control information 510 comprises pump drive control information 510B for controlling the pump drive 202, which can act, mechanically or otherwise, on the pump apparatus 112 of the cartridge 100 in order to convey fluid, in particular the sample P, through the fluid system 103 of the cartridge 100.

Alternatively, or additionally, the control information 510 comprises temperature-control apparatus control information 510C which specifies a temperature or a temperature curve or temperature profile of or for one or more temperature-control apparatus 204 of the analysis device 200, as a result of which the sample P or another substance contained in the fluid system 103 of the cartridge 100 can be temperature-controlled, in particular in order to carry out a PCR and/or hybridization.

Alternatively, or additionally, the control information 510 comprises execution information 511 for executing the test, in particular the sequence for controlling different actuators. The execution information 511 can also be separate from the control information 510, can be stored in the database 500 and/or can be transmitted to the analysis device 200 and/or the operating instrument 400.

Execution information 511 includes in particular delay information 511A, looping information 511B for repeating certain steps and/or condition information 511C for defining conditions, in particular threshold values, for triggering further steps or events.

The control information 510 can be in the form of a control file. The control information 510 preferably contains or can be represented as a command sequence which defines the execution of the test, in particular in a sequential or procedural manner. The analysis device 200 preferably comprises an interpreter for the control information 510.

The analysis device 200 and/or the control apparatus 207 preferably comprises a memory 207A in which the control information 510 is stored and/or temporarily stored or in which said information can be stored. In particular, it is provided that the analysis device 200 receives the control information 510 and, optionally, calibration information 520 and saves said information in the memory 207A. This makes it possible for the control apparatus 207 to control the analysis device 200 and/or actuators of the analysis device 200 independently and/or separately and/or disconnected from the operating instrument 400 in order to carry out or continue the test of the sample P.

The control apparatus 207 preferably controls and/or feedback controls and/or is designed to control and/or feedback control apparatus of the analysis device 200 in order to carry out the test.

The control apparatus 207 preferably comprises an actuator interface 207B by means of which one or more of the actuators can be controlled. In particular, the actuator interface 207B makes it possible to supply power to and/or to specify a target value for one or more of the actuators. This makes it possible to specify a target temperature value and/or a target temperature profile or curve for one or more of the temperature-control apparatus 204 by means of the actuator interface 207B. Alternatively, or additionally, the pump drive 202 can be controlled.

The pump drive 202 preferably comprises a stepper motor, as a drive element, and the actuator interface 207B preferably comprises a corresponding stepper motor controller. Owing to this combination, fluid can be conveyed in the fluid system 103 of the cartridge 100 in a very accurate manner. In addition, via the actuator interface 207B, the analysis device 200 and/or the control apparatus 207 can activate and/or supply power to one or more of the valve actuators 205, such that valves 115A, 115B located on the cartridge 100 can be opened and/or closed.

Alternatively or additionally, the analysis device 200, in particular the control apparatus 207, comprises a read-out module 207C for reading out measurement results 713 from the sensor apparatus 113. The read-out module 207C can be designed to digitalize measurement results 713 determined in the sensor apparatus 113 and to store and/or transmit said results in the form of a code or data set. In some cases, at least with regard to the digitalization of the measurement results, the read-out module 207C can also be located in the cartridge 100 or in the sensor apparatus 113, and/or the read-out module 207C can read out measurement results 713 digitalized by the sensor apparatus 113.

Alternatively, or additionally, the analysis device 200 and/or the control apparatus 207 can comprise an error module 207D for identifying errors. In particular, the error module 207D is designed to detect errors in the execution of the test. Alternatively, or additionally, the error module 207D can detect and document errors in boundary conditions, for example, a temperature, inclination or the like, and/or control the analysis device 200 according to and/or taking into account the error detection.

The analysis system 1, the cartridge 100 and/or the analysis device 200 is/are preferably designed to carry out the proposed method and/or the method is preferably controlled by means of the control information 510, taking into account the control information 510 or in a manner specified by the control information 510. However, the method described below can also be modified and the invention can also be used and be advantageous for other methods for testing an in particular biological sample.

Within the context of the method, a sample P having at least one analyte A on the basis of a fluid or a liquid from the human or animal body, in particular blood, saliva or urine, is usually first introduced into the receiving cavity 104 via the connection 104A, in order to detect diseases and/or pathogens, it being possible for the sample P to be pretreated, in particular filtered.

Once the sample P has been received, the receiving cavity 104 and/or the connection 104A thereof is fluidically closed, in particular in a liquid-tight and/or gas-tight manner.

Preferably, the cartridge 100 together with the sample P is then linked or connected to the analysis device 200, in particular is inserted or slid into the analysis device 200.

The method sequence, in particular the flow and conveying of the fluids, the mixing and the like, is controlled by the analysis device 200 or the control apparatus 207, in particular by accordingly activating and actuating the pump drive 202 or the pump apparatus 112 and/or the valve actuators 205 or valves 115A, 115B.

During the nucleic-acid assay, a desired volume of the sample P that is mixed and/or pretreated in the mixing cavity 107 is subsequently preferably fed to one or more reaction cavities 109A-C, particularly preferably via (respectively) one of the upstream, optional intermediate cavities 106A to 106C and/or with different reagents or primers, in this case dry reagents S4 to S6, being added or dissolved.

In the reaction cavities 109A-C, the amplification reactions or PCRs are carried out to copy/amplify the analytes A. This is carried out in particular by means of the assigned, preferably common, reaction temperature-control apparatus(es) 204A and/or preferably simultaneously for all the reaction cavities 109A-C, i.e., in particular using the same cycles and/or temperature (curves/profiles).

During the nucleic-acid assay, a label is in particular produced directly and/or during the amplification reaction(s) (in each case) and/or is attached to the analytes A and/or amplification products. This is in particular achieved by using corresponding, preferably biotinylated, primers. However, the label can also be produced and/or bonded to the analytes A and/or amplification products separately or later, optionally also only in a sensor compartment of the sensor apparatus 113 and/or after hybridization. In particular, during the protein assay, a label is only bonded to analytes A after hybridization of the analytes A to the capture molecules.

The label is used in particular for detecting bonded analytes A and/or amplification products. In particular, the label can be detected or the label can be identified in a detection process, as explained in greater detail in the following.

After carrying out the amplification reaction(s), corresponding fluid volumes and/or amplification products are conducted out of the reaction cavities 109A-C in succession to the sensor arrangement, in particular the sensor apparatus 113 and/or the sensor compartment, in particular via a group-specific and/or separate intermediate cavity 106E, 106F or 106G (respectively) and/or via the optional (common) intermediate temperature-control cavity 110.

After the sample P and/or the analytes A and/or amplification products are fed to the sensor apparatus 113, the analytes A and/or amplification products are hybridized to the capture molecules, preferably by (actively) temperature-controlling, in particular heating, the sensor arrangement or sensor apparatus 113, in particular by means of the sensor temperature-control apparatus 204C.

When carrying out the protein assay, the sample P or the analytes A is/are preferably fed directly from the mixing cavity 107 to the sensor arrangement or sensor apparatus 113 and/or is/are guided past the intermediate cavity/cavities 106A-G, reaction cavity/cavities 109A-C and/or the intermediate temperature-control cavity 110 via the bypass 114A.

Once the sample P, analytes A and/or amplification products are hybridized and/or bonded to the capture molecules, detection follows, in particular by means of the preferably provided label, or in another manner.

In the following, a particularly preferred variant of the detection is described in greater detail, specifically electrochemical detection, but other types of detection, for example optical detection, capacitive detection or the like, may also be carried out.

Following the (respective) bondings/hybridizations, preferably an optional washing process takes place and/or additional reagents or liquids, in particular from the storage cavities 108B to 108E, are optionally fed in.

Subsequently and/or after the washing process, in accordance with a preferred variant of the method, detection of the analytes A and/or amplification products bonded to the capture molecules takes place.

If the bonded analytes A or amplification products are still not marked or provided with a label, in particular during the protein assay, the labels are then fed to the sensor arrangement or the sensor compartment, preferably from the storage cavity 108E. Optionally, there is then another washing process.

In order to detect the analytes A or amplification products bonded to the capture molecules, a reagent F4 and/or detector molecules, in particular alkaline phosphatase/streptavidin, is/are fed to the sensor apparatus 113, preferably from the storage cavity 108D.

Within the meaning of the present invention, the term "detector molecules" is preferably understood to mean molecules that bond specifically to the marker or label of the (bonded) analytes A or amplification products and thus allow the detection thereof.

In particular, the detector molecules may be enzyme conjugates and/or immunoconjugates, which bond specifically to the marker or label, in particular biotin, and comprise a reporter enzyme for converting a substrate.

In the context of the present invention, the detector molecules are preferably based on streptavidin, which has a high affinity for biotin, and/or alkaline phosphatase, which can convert non-reactive phosphate monoesters to electrochemically active molecules and phosphate.

Preferably, a detection system is used, where the label is based on biotin and where the detector molecules are based on streptavidin/alkaline phosphatase. However, other detector molecules can also be used.

The reagents F4 or detector molecules can bond to the bonded analytes or amplification products, in particular to the label of the bonded analytes A or amplification products, particularly preferably to the biotin marker.

Optionally, subsequently or after the reagents F4 and/or detector molecules have bonded to the analytes A and/or amplification products and/or the labels, an (additional) washing process and/or flushing takes place, preferably by means of the fluid or reagent F3 or wash buffer, in particular in order to remove unbonded reagents F4 and/or detector molecules from the sensor apparatus 113.

Preferably, a reagent S8 and/or substrate for the detection, in particular from the storage cavity 106D, is lastly fed to the sensor arrangement or sensor apparatus 113, preferably together with a fluid or reagent F2 (in particular a buffer), which is suitable for the substrate, particularly preferably for dissolving the reagent S8 and/or substrate, the fluid or reagent in particular taken from the storage cavity 108B.

Preferably, p-aminophenyl phosphate (pAPP) is used as the substrate.

The substrate preferably reacts on and/or with the bonded analytes A or amplification products and/or detector molecules and/or allows these to be electrochemically measured.

Preferably, a first or electrochemically active substance is detected in the sensor apparatus 113 by electrochemical measurement and/or redox cycling.

The measurement is preferably taken just once and/or for the entire sensor array 113A of the sensor apparatus 113 and/or for all the sensor fields 113B of said sensor array, in particular simultaneously or in parallel. In particular, the bonded analytes A or amplification products are detected, identified or determined simultaneously or in parallel in a single or common detection process.

However, in principle, it is also possible to measure a plurality of sample portions in the sensor apparatus 113 or in a plurality of sensor apparatus 113 in succession or separately.

The test results or measurement results 713 are in particular electrically transmitted to the analysis device 200 or the control apparatus 207 thereof, preferably by means of the electrical connection apparatus 203, and are accordingly prepared, analyzed, evaluated, stored, displayed and/or output, in particular by the display apparatus 209 and/or interface 210.

After the test has been carried out, the cartridge 100 is disconnected from the analysis device 200 and/or is released or ejected therefrom, and is in particular disposed of.

The test results or measurement results 713 that have been determined by means of the testing method described above or by means of another testing method are transmitted, in particular electrically, to the analysis device 200 and/or the control apparatus 207 thereof, preferably by means of the electrical connection apparatus 203. The measurement results 713 are transmitted from or via the analysis device 200 preferably to the operating instrument 400, and are prepared, analyzed, evaluated, stored, displayed and/or output by the operating instrument 400.

The measurement result(s) 713 of the sensor apparatus 113 is/are preferably transmitted from the cartridge 100 to the analysis device 200 and/or retrieved by the analysis device 200 from the cartridge 100 and/or the sensor apparatus 113. For this purpose, the analysis system 1 is preferably designed to transmit the measurement result 713 from the sensor apparatus 113 of the cartridge 100, from the analysis device 200 and/or via the analysis device 200 to the operating instrument 400. This is indicated in FIG. 4 by the arrow 607, which corresponds to the results retrieval from the cartridge 100 by the analysis device 200.

In one aspect of the present invention, which can also be implemented independently, the measurement result(s) 713, i.e., in particular the result for the test of the sample P using the analysis device 200, is/are preferably transmitted to the operating instrument 400 without any prior evaluation or can be transmitted without any prior evaluation. This is indicated in FIG. 4 by the arrow 608, which corresponds to the data transmission from the analysis device 200 to the operating instrument 400.

Transmitting the measurement results 713 without any prior evaluation in the analysis device 200 makes possible an individual and/or easily adaptable evaluation outside of the analysis device 200.

Transmission of the measurement result 713 without any prior evaluation can also be referred to as the transmission of unprocessed measurement results 713. This should be understood to mean that, although it is possible to carry out processing in terms of data transmission, as provided for by transmission protocols, in order to address transmission errors or the like, it is not provided that the measurement results 713 are interpreted prior to transmission, i.e., the significance of measurement results is not determined or established and, if applicable, conclusions are not made with regard to properties of the sample P. In the present case of a biological sample P, this means in particular that measurement results 713 are assigned to the presence of certain substances/analytes and/or concentrations and/or diseases or the like not in the analysis device 200, but rather externally.

The measurement results 713 are preferably evaluated in the operating instrument 400 after the operating instrument 400 has received the measurement results 713 from the analysis device 200 and/or the cartridge 100. In FIG. 4, the evaluation process by means of the operating instrument 400 is indicated by the arrow 609.

The evaluation of the measurement results 713 by means of the operating instrument 400 can also be carried out independently and/or separately and/or disconnected from the analysis device 200.

As mentioned previously, the operating instrument 400 can determine and/or retrieve, in particular from the database 500, evaluation information 530 on the basis of the cartridge identifier 100C and/or the device identifier 200C. The evaluation information 530 is designed or used to evaluate measurement results 713 determined during the test. The measurement results 713 can be evaluated by the operating instrument 400 on the basis of or using said evaluation information 530. For this purpose, the operating instrument 400 is preferably designed to retrieve and/or receive measurement results 713 from the analysis device 200.

In one aspect of the present invention, which can also be implemented independently, the operating instrument 400 evaluates or is designed to evaluate the measurement results 713 using the evaluation information 530 and independently and/or separately and/or disconnected from the analysis device 200. It is also possible for the data connection DVA between the analysis device 200 and the operating instrument 400 to be disconnected, terminated or broken after the measurement results 713 have been retrieved, and for the evaluation to also be carried out separately and/or disconnected from the analysis device 200.

In particular, the evaluation information 530 comprises instructions, in particular an algorithm, in order to compute or calculate with the measurement results 713 and to assign said measurement results 713 to a physical variable, value or property. As a result, the measurement results 713 can be interpreted.

The evaluation information 530 is preferably individual, unique and/or specific to a specific cartridge 100 or batch of cartridges 100 and/or to a specific analysis device 200 and/or the combination of a specific cartridge 100 and an analysis device 200. Alternatively or additionally, the evaluation information 530 is individual, unique and/or specific to a/the operating instrument 400, in particular an operating system of the operating instrument 400.

The evaluation information 530 is particularly preferably dependent on the specific sensor apparatus 113 of the respective cartridges 100 and can be specific to a specific type of cartridge or a specific batch of cartridges and/or a specific test or evaluation that can be carried out using a type of cartridge or a batch of cartridges.

The measurement results 713 can be evaluated by means of the operating instrument 400 on the basis of or using said evaluation information 530.

The evaluation information 530 preferably comprises (field) assignment information 531 which, in the case of a sensor apparatus 113 having a plurality of sensor fields 113B, assigns functions and/or properties to the measurement results 713 that correspond to the respective sensor fields 113B.

Alternatively, or additionally, the evaluation information 530 comprises interpretation information 532 which assigns certain properties of the sample P to measurement results 713. This interpretation information may be threshold values, or the interpretation information 532 comprises threshold values or the like.

Preferably, interpretation information 532 is available that relates to the respective sensor fields 113B and/or to the measurement results 713 corresponding thereto, and therefore the interpretation information 532 comprises the (field) assignment information 531 or vice versa.

The (field) assignment information 531 is particularly preferably dependent on the specific sensor apparatus 113 of the respective cartridges 100 and can be specific to a specific type of cartridge and/or a specific analysis that can be carried out using a type of cartridge. Alternatively or additionally, the same also applies to the interpretation information 532.

Different control information 510 and/or calibration information 520 and/or evaluation information 530 can be provided for the same cartridge 100, in particular when different tests can be carried out using the same cartridge 100, and the information corresponds to one of the tests that can be carried out, respectively.

The evaluation information 530 preferably comprises an assignment of the measurement results 713, which are preferably in the form of a value, a number, a code or the like, to a physical variable. As a result, the measurement results 713 can be interpreted.

The (field) assignment information 531 is preferably designed to assign each of the measurement results 713 from the respective sensor fields 113B to a property or a sensor type of the respective sensor fields 113B.

As mentioned at the outset, the evaluation information 530 preferably comprises instructions, which preferably form an algorithm and/or a plugin or module. This evaluation information 530 can form all or part of the evaluation module 440 of the operating instrument 400. For this purpose, the evaluation information 530 is integrated in the operating instrument 400 as a component or a module which defines the behavior of the evaluation module 440 and/or of the operating instrument 400.

The operating instrument 400 implements the evaluation information 530 preferably by interpreting the instructions using a processor or controller of the operating instrument 400. The instructions are in particular source code, pre-compiled code or machine code for being executed on the operating instrument 400.

The evaluation information 510 is preferably specific to a certain group of operating instruments 400, in particular specific to a certain operating system or a group of operating systems.

Depending on the operating instrument identifier 400C for identifying an operating instrument 400 or group, class or kind of operating instruments 400, in particular having the same operating system, it is possible to provide, make available and/or retrieve different forms of the same or different evaluation information 510. In particular, when transmitting the operating instrument identifier 400C, the database 500 sends evaluation information 510 of such kind back to the operating instrument 400, that can be processed, compiled, used and/or executed by the operating instrument 400.

The analysis system 1, in particular the database 500, therefore preferably comprises different items of evaluation information 530 or is designed to generate and/or provide different items of evaluation information 530, the different items of evaluation information 530 generating or making possible the same or similar functionality on different operating instruments 400. Nevertheless, the evaluation information 530 is preferably specific to a cartridge 100 or a batch of cartridges 100.

As a result, different items of evaluation information 530 are preferably provided and/or can be retrieved for different cartridges 100 or batches of cartridges 100, and said different items of evaluation information 530 are each provided and/or can each be retrieved in different versions for different operating instruments 400.

The operating instrument 400 preferably outputs or is designed to output, by means of the output apparatus 410, the evaluation results 740 that are determined, in particular calculated, by evaluating the measurement results 713 using the evaluation information 530. For this purpose, the operating instrument 400 can display the evaluation results 740 graphically or otherwise, in particular by means of the screen or display 411. Alternatively, or additionally, the operating instrument 400 sends or is designed to send the evaluation results 740 to the database 500.

The operating instrument 400 is preferably designed to transmit, to the analysis device 200, control information 510 for receiving or ejecting the cartridge 100. Alternatively or additionally, the operating instrument 400 is designed to transmit control information 510 for starting the test to the analysis device 200. Alternatively or additionally, the operating instrument 400 is designed to retrieve and/or receive measurement results 713 from the analysis device 200.

The operating instrument 400 is preferably designed to receive and/or display an operating status of the analysis device 200.

In particular, the operating instrument 400 comprises a graphical user interface which is displayed on the screen or display 411. The graphical user interface preferably comprises an interface which graphically symbolizes the possible controls and/or states of the analysis device 200. Alternatively, or additionally, the user interface is designed to control interaction with the database 500 and/or with the analysis device 200. For this purpose, the operating instrument 400 can be designed so as to be touch-sensitive, in particular via a touch-sensitive screen or display 411. Alternatively, or additionally, the user interface can however also be controlled via the touchpad 422, the microphone 423, the keyboard 424 or some other input apparatus 420.

In one aspect of the present invention, the analysis system 1 comprises a plurality of cartridges 100 which support the same or different tests. It is therefore possible for there to be a plurality of different types of cartridge for carrying out different tests and/or for the analysis system 1 to comprise or support said types of cartridge. It is preferable for these cartridges 100 to be inserted into the same analysis device 200 and/or for the test using the cartridges 100 to be carried out or be able to be carried out by means of the same analysis device 200.

In another aspect, the proposed analysis system 1 comprises a plurality of analysis devices 200. It is preferable that the analysis devices 200 can each be coupled to the same operating instrument 400. The same operating instrument 400 can thus be connected to different analysis devices 200, the data connection DVA preferably connecting to or being established to just one of the analysis devices 200 at any one time. Alternatively, the same operating instrument 400 can however also be connected to a plurality of analysis devices 200 simultaneously. In this case, it is preferable for the operating instrument 400 to assist in selecting an analysis device 200 for configuration and/or control. In particular, an analysis device 200 can be selected by the operating instrument 400 via the input apparatus 420, such that (only) the selected analysis device 200 is subsequently controlled.

The analysis system 1 can comprise or support a plurality of operating instruments 400. In particular, a plurality of operating instruments 400 can be coupled to the same analysis device 200 alternately, but preferably not simultaneously. By coupling the analysis device 200 to an operating instrument 400, the data connection DVA between the analysis device 200 and the operating instrument 400 is preferably established, such that control information 510 can be transmitted to the analysis device 200 and/or results can be transmitted to the operating instrument 400.

The database 500 preferably comprises a plurality of different items of control information 510 for carrying out tests using the different cartridges 100 and/or different analysis devices 200. The control information 510 can also be formed in multiple parts. In particular, the control information 510 can comprise parts specific to the cartridge 100 and parts specific to the analysis device 200.

The analysis device 200 can preferably be calibrated and/or configured by calibration information 520 that can form part of the control information 510 or can be provided separately. For this purpose, the calibration information 520 can be determined, retrieved and/or transmitted to the analysis device 200 by means of the operating instrument 400.

In one example, fluid sensor calibration information 521 is provided which influences setting and/or evaluation of the fluid sensor 206A. The fluid sensor calibration information 521 is preferably dependent on the test to be carried out.

In another aspect of the present invention, which can also be implemented independently, a computer program product is provided that comprises program code means for carrying out the proposed method. The computer program product is in particular an instruction stored on a storage medium, in particular in the form of a smartphone app or the like, which is set up to determine and/or receive the cartridge identifier 100C. Alternatively or additionally, said instruction is designed to transmit the cartridge identifier 100C to the database 500 and to subsequently receive control information 510 from the database 500. Alternatively, or additionally, said instruction is designed to transmit or forward control information 510 to the analysis device 200. Alternatively, or additionally, said instruction is designed to receive, evaluate and/or interpret measurement results 713, in particular using retrieved and/or received evaluation information 530.

Evaluating the measurement results 713 preferably comprises assigning measurement results 713 corresponding to particular sensor fields 113B to functions of the respective sensor fields 113B. This can be achieved by using different evaluation methods, threshold values or the like for different sensor fields 113B.

It is possible for sensor fields 113B of the same kind to be evaluated together. In this case, it is preferable that measurement results 713 corresponding to sensor fields 113B of the same kind are tested for considerable deviations, that measurement results 713 having considerable deviations with respect to other measurement results 713 for sensor fields 113B of the same kind are rejected, and that only similar measurement results 713 for sensor fields 113B of the same kind are evaluated.

During evaluation, it is possible to determine measurement results 713 for sensor fields 113B of the same kind. Alternatively, or additionally, the measurement results 713, jointly or in a calculated manner, for example, the average value thereof, can be compared with a threshold value or with a plurality of threshold values, or evaluated in some other way. In this case, the one or more threshold values may be values or, alternatively or additionally, specified profile or curve progressions, specified gradients, maximum values thereof or the like.

By evaluating the measurement results 713, the evaluation result 740 is generated, which preferably corresponds to a physical value, variable or property of the sample P, preferably directly. For example, the evaluation result 740 represents the presence of certain DNA sequences and/or RNA sequences and/or proteins, in particular antigens and/or antibodies.

Alternatively, or additionally, the evaluation result 740 can however also be or comprise an interpretation derived from the presence of the DNA sequences and/or RNA sequences and/or proteins, in particular antigens and/or antibodies, in particular information on whether or how likely it is that a certain disease and/or pathogen, such as a virus, bacterium or the like, is present in the sample P.

The evaluation result 740 is preferably output by the output apparatus 410 of the operating instrument 400, or can be output, in particular displayed, by the output apparatus 410.

If a disease and/or a pathogen is detected, it can be provided that the operating instrument 400 automatically outputs or sends a warning and/or message.

Measurement results 713 and/or evaluation results 740 are preferably archived. Particularly preferably, these results are saved, or saved temporarily, in the operating instrument 400. Alternatively, or additionally, these results are saved and/or archived in the database 500, in particular in the results memory 550 of the database 500. For this purpose, the evaluation results 740 can be transmitted from the operating instrument 400 to the database 500 via data transmission 610.

Archiving in the database 500 can be temporally offset with respect to the evaluation results 740 being generated and/or the measurement results 713 being retrieved or received. This is in particular the case when the test or evaluation is carried out without there being a data connection DVD between the database 500 and the operating instrument 400. In this case, the measurement results 713 and/or evaluation results 740 can be transmitted to the database 500 in a temporally offset manner and/or at a later point in time, as soon the data connection DVD is restored or can be re-established.

Control information 510 and/or calibration information 520 and/or evaluation information 530 can be retrieved from the database 500 separately, disconnected and/or independently from the analysis device 200. For this purpose, a data connection DVB between the cartridge 100 and the operating instrument 400 is preferably used, for example by the operating instrument 400 reading in the barcode 124 and determining the cartridge identifier 100C by evaluation. This is also possible when the data connection DVA between the analysis device 200 and the operating instrument 400 is disconnected, terminated or broken.

Furthermore, the operating instrument 400 can also retrieve control information 510, calibration information 520 and/or evaluation information 530 from the database 500 independently, disconnected and/or separately from the cartridge 100 and/or the analysis device 200. It is therefore possible for example for the operating instrument 400 to firstly determine, read out or receive the cartridge identifier 100C. Retrieval from the database 500 can take place subsequently, also independently from the cartridge 100 and/or the analysis device 200. For this purpose, in particular only the data connection DVD between the operating instrument 400 and the database 500 is required. The retrieved data can be stored temporarily in the memory 450.

It is preferable for the analysis device 200 to determine or read out the cartridge identifier 100C and send it to the operating instrument 400 before the test is carried out using a specific cartridge 100, even if the operating instrument 400 has already previously retrieved or received control information 510, calibration information 520 and/or evaluation information 530. The cartridge identifier 100C transmitted from the analysis device 200 to the operating instrument 400 before the test has begun can then be checked by the operating instrument 400 in order to determine whether control information 510, calibration information 520 and/or evaluation information 530 that corresponds to the cartridge 100 and/or the cartridge identifier 100C is provided, in particular already stored or temporarily stored in the memory 450.

If the operating instrument 400 identifies control information 510 and/or calibration information 520 that already corresponds to the cartridge 100 or the cartridge identifier 100C, this information can be transmitted to the analysis device 200 and the test using the cartridge 100 inserted into the analysis device 200 can be started.

Alternatively, required control information 510 and/or calibration information 520 is retrieved from the database 500.

In a preferred development of the invention, the analysis system 1 comprises a plurality of different cartridges 100 for carrying out preferably different tests, to which different control information 510 and evaluation information 530 corresponds.

For the same cartridge 100, different control information 510 and/or evaluation information 530 can be provided, selected, selectable, retrieved, retrievable, used and/or usable, in particular when different tests can be carried out using the same cartridge 100, and the control information 510 corresponds in each case to one of the tests that can be carried out.

In another aspect of the present invention, which can also be implemented independently, a computer program product is provided that comprises program code means for carrying out the proposed method. This computer program product is in particular an instruction stored on a storage medium, in particular in the form of a smartphone app or the like.

The instruction is preferably set up to control the operating instrument 400, and/or to determine and/or receive the cartridge identifier 100C.

Alternatively, or additionally, the instruction is set up to control the operating instrument 400, to transmit the cartridge identifier 100C to the database 500, and to subsequently receive control information 510 from the database 500.

Alternatively, or additionally, the instruction is designed to control the operating instrument 400 and/or to transmit or forward control information 510 to the analysis device 200.

Alternatively, or additionally, the instruction is designed to control the operating instrument 400, and/or to receive, evaluate and/or interpret measurement results 713, in particular using retrieved and/or received evaluation information 530.

In general, the analysis device 200, the cartridge 100 or in particular the sensor apparatus 113 may measure, detect or identify the one or more analytes A by means of specific bonding, in particular by means of capture molecules and/or of means of electrochemical detection such as redox cycling, or the like, preferably performed on the cartridge 100 and/or in the sensor apparatus 113. Preferably, the capture molecules are arranged or immobilized on a sensor array or on sensor fields or electrodes of the sensor apparatus 113. In particular, an immuno-assay or a protein assay for detecting or identifying a protein and/or a nucleic-assay for detecting or identifying a nucleic-acid sequence can be or is realized.

Alternatively, or additionally, measurements without specific bonding and/or without electrochemical detection can be used or performed, preferably in or by the analysis device 200 and/or cartridge 100. Such measurements can include an optical measurement, impedance measurement, capacitance measurement, spectrometric measurement, mass spectrometric measurement, or the like. For this purpose, the analysis device 200 or cartridge 100 may comprise an optical spectrometer and/or allow optical measurements of the treated or untreated sample P. Thus, it is possible to measure, detect or identify other or further analytes A, compounds, material characteristics, or the like of the sample P, e.g. within the cartridge 100 or any other sample carrier. These alternative or additional measurements can be used or processed and/or evaluated in a similar manner as described or differently.

In particular, the present invention relates also to any one of the following aspects which can be realized independently or in any combination, also in combination with any aspects described above or in the claims.

1. Analysis system 1 for testing an in particular biological sample P,
the analysis system 1 comprising a cartridge 100 for receiving the sample P, and
the analysis system 1 comprising an analysis device 200 for receiving the cartridge 100 and subsequently carrying out the test using the received cartridge 100,
characterized
in that the analysis system 1 comprises an operating instrument 400 which preferably can be separated from the analysis device 200 with respect to a data connection and/or wirelessly connected to the analysis device 200,
   the operating instrument 400 being designed to determine or receive a cartridge identifier 100C corresponding to the cartridge 100 and, using this cartridge identifier 100C, to retrieve from a database 500 control information 510 for carrying out the test and/or to transmit said control information 510 to the analysis device 200; and/or
   the operating instrument 400 being designed to transmit to the analysis device 200 control information 510 for carrying out the test supported by the cartridge 100, and the analysis device 200 being designed to carry out the test using the transmitted control information 510 independently and/or separately from the operating instrument 400; and/or
   the analysis device 200 being designed to receive control information 510 from the operating instrument 400, to control the test of the sample P in the cartridge 100 using the control information 510 and to transmit measurement results 713 determined during the test to the operating instrument 400 without any prior evaluation; and/or
   the operating instrument 400 being designed to determine or receive a cartridge identifier 100C corresponding to the cartridge 100 and, using the cartridge identifier 100C, to retrieve from a database 500 evaluation information 530 for evaluating measurement results 713 determined during the test, and to evaluate the measurement results 713 using the evaluation information 530 independently and/or separately from the analysis device 200.

2. Analysis system according to aspect 1, characterized in that the cartridge 100 comprises a memory means 100D from which the cartridge identifier 100C can be read out, preferably electronically, in particular by means of the analysis device 200, and/or optically, preferably by means of a camera 421 of the operating instrument 400, the operating instrument 400 preferably being designed to automatically retrieve from the database 500 the control information 510 for controlling the analysis device 200 in order to carry out the test supported by the cartridge 100 and/or analysis information 530 for evaluating measurement results 713 determined by the test, by the cartridge identifier 100C of the cartridge 100 being read out or after the cartridge identifier 100C has been read out.

3. Analysis system according to aspect 1 or 2, characterized in that the control information 510 and/or the evaluation information 530 comprises instructions, preferably in the form of an algorithm, and/or the instructions forming a module which can be implemented by the analysis device 200 and/or the operating instrument 400, as a result of which the behavior of the analysis device 200 and/or of the operating instrument 400 can be changed.

4. Analysis system according to any one of the preceding aspects, characterized in that the analysis device 200 is designed to control apparatus of the analysis device 200 using the control information 510
   such that the sample P is conveyed inside the cartridge 100 to a sensor apparatus 113 in a manner specified by the control information 510, and/or
   such that valves 115 of the cartridge 100 are opened or closed in a manner specified by the control information 510, and/or
   such that one or more temperature-control apparatus 204 of the analysis device 200 are controlled such that the sample P and/or a sensor apparatus 113 is temperature-controlled in a manner specified by the control information 510.

5. Analysis system according to any one of the preceding aspects, characterized in that the analysis device 200 comprises:
   a receiver 210A for, preferably wirelessly, receiving the control information 510 from the operating instrument 400, and/or
   memory 207A for storing the control information 510, and/or
   a control apparatus 207 for controlling and/or feedback controlling apparatus of the analysis device 200 in order to carry out the test, and/or
   a connection apparatus 203 for establishing an electronic connection to a sensor apparatus 113 of the cartridge 100, and/or
   a read-out module 207C for reading out measurement results 713 from the sensor apparatus 113 of the cartridge 100, and/or
   a transmitter 210B for transmitting measurement results 713 read out from the sensor apparatus 113 to the operating instrument.

6. Analysis system according to any one of the preceding aspects, characterized in that the operating instrument 400 comprises an evaluation module 440 which is designed to evaluate measurement results 713 read out from the sensor apparatus 113, preferably by means of the evaluation information 530 retrieved from the database 500.

7. Analysis system according to any one of the preceding aspects, characterized in that the evaluation information 530 comprises interpretation information 532 which assigns the measurement results 713 to physical variables such that the measurement results 713 can be interpreted.

8. Analysis system according to any one of the preceding aspects, characterized in that the sensor apparatus 113 comprises a plurality of sensor fields 113B and the evaluation information 530 comprises assignment information 531 for assigning each of the measurement results 713 from the respective sensor fields 113B to a property of the or a sensor type of the respective sensor fields 113B.

9. Analysis system according to any one of the preceding aspects, characterized in that the operating instrument 400 comprises an output apparatus 410, preferably a display apparatus, in particular a display 411, and is designed to output evaluation results 740 that are determined, in particular calculated, by evaluating the measurement results 713 using the evaluation information 530.

10. Analysis system according to any one of the preceding aspects, characterized in that the operating instrument 400 is designed to
   transmit, to the analysis device 200, control information 510 for receiving or ejecting the cartridge 100, and/or transmit control information 510 to the analysis device 200 for starting the test, and/or
   retrieve and/or receive measurement results 713 from the analysis device 200, and/or
   send evaluation results 740 to a database 500.

11. Analysis system according to any one of the preceding aspects, characterized in that the operating instrument 400 comprises an input apparatus 420, in particular a touch-sensitive screen, by means of which the transmission of commands and/or information to the analysis device 200 can be triggered; and/or in that the operating instrument 400 and the analysis device 200 each comprise a wireless data interface 430, 210 which are designed to jointly establish an ad-hoc data connection between the operating instrument 400 and the analysis device 200, preferably such that, when the operating instrument 400 and the analysis device 200 approach one another in space, the data connection (DVA) therebetween is automatically established and is preferably displayed by means of the operating instrument 400.

12. Analysis system according to any one of the preceding aspects, characterized in that the operating instrument 400 comprises different interfaces 430 that are independent of one another for establishing data connections (DVA, DVD) to the analysis device 200 and to the database 500, the analysis device 200, as a peripheral device of the operating instrument 400, being designed to communicate exclusively with or via the operating instrument 400.

13. Analysis system according to any one of the preceding aspects, characterized in that the analysis system 1 comprises a plurality of different cartridges 100 for carrying out preferably different tests to which different control information 510 and evaluation information 530 corresponds.

14. Method for testing, in particular, a biological sample P by means of an analysis system 1, the analysis system 1 comprising a cartridge 100 for receiving the sample P, the cartridge 100 comprising a sensor apparatus 113 for measuring sample-specific measurement results and a fluid system for conveying the sample P to the sensor apparatus 113, the analysis system 1 comprising an analysis device 200 for receiving the cartridge 100 and subsequently carrying out the test using the received cartridge 100,
characterized
in that the analysis system 1 comprises an operating instrument 400 which preferably can be separated from the analysis device 200 with respect to a data connection and/or wirelessly connected to the analysis device 200,
the operating instrument 400 determining or receiving a cartridge identifier 100C corresponding to the cartridge 100 and, using the cartridge identifier 100C, retrieving from a database 500 control information 510 for carrying out the test and/or transmitting said control information 510 to the analysis device 200; and/or
the operating instrument 400 transmitting to the analysis device 200 control information 510 for carrying out the test supported by the cartridge 100, and the analysis device 200 carrying out the test using the transmitted control information 510 independently and/or separately from the operating instrument 400; and/or
the analysis device 200 receiving control information 510 from the operating instrument 400, controlling the test of the sample P in the cartridge 100 using the control information 510 and transmitting measurement results 713 determined during the test to the operating instrument 400 without any prior evaluation; and/or
the operating instrument 400 determining or receiving a cartridge identifier 100C corresponding to the cartridge 100 and, using the cartridge identifier 100C, retrieving from a database 500 evaluation information 530 for evaluating measurement results 713 determined during the test, and evaluating the measurement results 713 using the evaluation information 530 independently and/or separately from the analysis device 200.

15. Computer program product comprising program code means which, when executed, cause the method steps of the method according to the preceding aspect to be carried out.

16. Method for testing, in particular, a biological sample P by means of an analysis system 1,
the analysis system 1 comprising a cartridge 100 for receiving the sample P,
the analysis system 1 comprising an analysis device 200 for receiving the cartridge 100 and subsequently carrying out the test using the received cartridge 100,
wherein the analysis system 1 comprises an operating instrument 400 which is separable from the analysis device 200 with respect to a data connection and/or wirelessly connectable to the analysis device 200,
the operating instrument 400 determining or reading out a cartridge identifier 100C corresponding to the cartridge 100 and, using the cartridge identifier 100C, retrieving from a database 500 control information 510 for carrying out the test and transmitting said control information 510 to the analysis device 200.

17. Method for testing, in particular, a biological sample P by means of an analysis system 1, preferably according to aspect 16,
the analysis system 1 comprising an analysis device 200 for receiving the cartridge 100 and subsequently carrying out the test using the received cartridge 100,
wherein the analysis system 1 comprises an operating instrument 400 which is separable from the analysis device 200 with respect to a data connection and/or wirelessly connectable to the analysis device 200,
the operating instrument 400 retrieving from an external database 500 control information 510 for controlling actuators 202, 204, 205 of the analysis device 200 for carrying out the test supported by the cartridge 100 and transmitting to the analysis device 200 said control information 510, and the analysis device 200 carrying out the test using the transmitted control information 510 independently, disconnected and/or separately from the operating instrument 400.

18. Method for testing an in particular biological sample P by means of an analysis system 1, preferably according to aspect 16 or 17,
the analysis system 1 comprising an analysis device 200 for receiving the cartridge 100 and subsequently carrying out the test using the received cartridge 100,
wherein the analysis system 1 comprises an operating instrument 400 which is separable from the analysis device 200 with respect to a data connection and/or wirelessly connectable to the analysis device 200,
the analysis device 200 receiving control information 510 from the operating instrument 400, controlling the test of the sample P in the cartridge 100 using the control information 510 and transmitting measurement results 713 determined during the test to the operating instrument 400 without any prior evaluation.

19. Method for testing, in particular, a biological sample P by means of an analysis system 1, preferably according to any one of aspects 16 to 18,
the analysis system 1 comprising an analysis device 200 for receiving the cartridge 100 and subsequently carrying out the test using the received cartridge 100,
wherein the analysis system 1 comprises an operating instrument 400, the operating instrument 400 determining, reading out or receiving a cartridge identifier 100C corresponding to the cartridge 100 and, using the cartridge identifier 100C, retrieving from a database 500 evaluation information 530 for evaluating measurement results 713 determined during the test, and evaluating the measurement results 713 using the evaluation information 530 independently, disconnected and/or separately from the analysis device 200.

20. Computer program product comprising program code means which, when executed, cause the method steps of the method according to any one of aspects 16 to 19 to be carried out.

Individual aspects and features of the present invention and individual method steps and/or method variants may be implemented independently from one another, but also in any desired combination and/or order.

The invention claimed is:

1. Analysis system for testing a biological sample, comprising:
  a cartridge for receiving the sample, said cartridge having a sensor apparatus configured to obtain measurement results from testing of the sample received in the cartridge, the cartridge further including electrical contacts from which the measurement results from the testing the sample can be read out or transmitted to an analysis device;
    said sensor apparatus having a memory inside the sensor apparatus in which a cartridge identifier corresponding to the cartridge is stored, and said sensor apparatus comprises a chip having electrochemical detection electrodes for detecting at least one analyte of the sample;
  the analysis device is configured to receive the cartridge and subsequently carry out the testing of the sample received inside the received cartridge, said the analysis device further comprises a connection apparatus with electrical contact elements configured to establish an electronic connection to the sensor apparatus via the contacts on the cartridge, and;
  an operating instrument which is connected to the analysis device by a disconnectable data interface connection,
  wherein the operating instrument is configured to retrieve the cartridge identifier corresponding to the cartridge from said memory of the sensor apparatus via said data interface connection and to use the cartridge identifier to retrieve control information from a database for carrying out the testing of the sample received in the cartridge and to transmit said control information to the analysis device,
  wherein the analysis device is configured to carry out the testing of the sample received in the cartridge using said control information transmitted from the operating instrument and to read out the measurement results from the sensor apparatus via the same connection apparatus by which the cartridge identification is read out from the memory.

2. Analysis system according to claim 1, wherein the analysis device is configured to read out said or a different cartridge identifier.

3. Analysis system according to claim 1, wherein the control information comprises a set of instructions that are contained in a software module which can be implemented by the analysis device, as a result of which the behavior of the analysis device is changeable or changed.

4. Analysis system according to claim 1, further comprising a receiver for wirelessly receiving the control information from the operating instrument.

5. Analysis system according to claim 1, wherein the operating instrument comprises an input apparatus by means of which the transmission of at least one of commands or information to the analysis device is triggerable.

6. Analysis system according to claim 1, wherein the operating instrument comprises different interfaces that are independent of one another for establishing data connections to the analysis device and to the database, the analysis device, as a peripheral device of the operating instrument, being configured to communicate exclusively with or via the operating instrument.

7. Analysis system according to claim 1, wherein the analysis system comprises either said at least one cartridge being configured for carrying out a plurality of different tests controlled by respective pieces of control information, or said at least one cartridge comprises a plurality of different cartridges each of which is configured for carrying out a respective one of a plurality of different tests controlled by respective different pieces of control information.

8. Analysis system according to claim 1, wherein the control information comprises a set of instructions that are contained in a software module which can be implemented by the operating instrument, as a result of which operation of the operating instrument is changed or changeable.

9. Analysis system according to claim 1, wherein the operating instrument is configured to send evaluation results to the at least one database.

10. Analysis system according to claim 1, wherein said operating instrument is separable from the analysis device with respect to the at least one database.

11. Analysis system according to claim 1, wherein the analysis system comprises said at least one cartridge being configured for carrying out different tests or said at least one cartridge comprises a plurality of different cartridges configured for carrying out different tests, wherein different pieces of evaluation information correspond to one or more of said different tests or to measurement results resulting therefrom.

* * * * *